US008260779B2

(12) United States Patent
Hudgins et al.

(10) Patent No.: US 8,260,779 B2
(45) Date of Patent: Sep. 4, 2012

(54) SYSTEMS, METHODS, AND APPARATUS FOR AUTOMATED MAPPING AND INTEGRATED WORKFLOW OF A CONTROLLED MEDICAL VOCABULARY

(75) Inventors: Darren S. Hudgins, Sandy, UT (US);
Thomas A. Oniki, South Jordan, UT (US)

(73) Assignee: General Electric Company, Schenectady, NY (US)

( * ) Notice: Subject to any disclaimer, the term of this patent is extended or adjusted under 35 U.S.C. 154(b) by 392 days.

(21) Appl. No.: 12/561,547

(22) Filed: Sep. 17, 2009

(65) Prior Publication Data

US 2011/0066425 A1 Mar. 17, 2011

(51) Int. Cl.
*G06F 7/00* (2006.01)
(52) U.S. Cl. ........................................ 707/736; 707/749
(58) Field of Classification Search .................. 707/736, 707/749, 755, 740, 748
See application file for complete search history.

(56) References Cited

U.S. PATENT DOCUMENTS

| 7,840,589 B1* | 11/2010 | Holt et al. ................. 707/769 |
| 2002/0059161 A1* | 5/2002 | Li ................................ 707/1 |
| 2006/0136194 A1* | 6/2006 | Armstrong et al. ............. 704/4 |

OTHER PUBLICATIONS

B. Hieb, MD, "Controlled Medical Vocabulary in the CPR Generations," Gartner, Inc, Tutorials, TU-20-1272, Nov. 5, 2003 (5 pages).*
B. Hieb, MD, "Controlled Medical Vocabulary in the CPR Generations," Gartner, Inc., Tutorials, TU-20-1272, Nov. 5, 2003 (5 pages).

* cited by examiner

*Primary Examiner* — Angela Lie
(74) *Attorney, Agent, or Firm* — Hanley, Flight & Zimmerman, LLC

(57) ABSTRACT

Systems, methods, and apparatus provide clinical terminology services including a controlled medical vocabulary supplemented by local clinical content. An example method includes accessing an initial controlled medical vocabulary including at least one external terminology via a vocabulary management server; processing local clinical content including unstructured local clinical content provided via an importer framework; analyzing and extracting the unstructured local clinical content using a text analyzer and extraction tool to generate one or more proposed terms; identifying one or more synonyms for the one or more proposed terms and placing the one or more synonyms into a queue to be added to the controlled medical vocabulary; reviewing the one or more synonyms; and adding one or more synonyms to the controlled medical vocabulary with placement and relationship based on analyzing unstructured local clinical content to automatically map between the at least one external terminology and the local clinical content.

20 Claims, 19 Drawing Sheets

Terminology/Management Inbox

| From | Subject | Received | Click to Execute |
|------|---------|----------|------------------|
| Smith, Bill | Proposed Changes to problem List Domain | Wed 4/29/09 1:42:03 PM | ↻ Approve  ⊗ Reject  ⓘ View Details |
| Smith, Bill | Proposed Changes to Gender Concepts | Wed 4/29/09 1:41:59 PM | ↻ Approve  ⊗ Reject  ⓘ View Details |
| Chambers, Alice | Proposed Mappings From ICD-9 to ICD-10 | Tue 4/28/09 8:11:13 AM | ↻ Approve  ⊗ Reject  ⓘ View Details |
| Automated Mapping Assistant (Rule 1021) | New mappings identified | Mon 4/27/09 11:01:23 PM | ↻ Approve  ⊗ Reject  ⓘ View Details |
| Automated Mapping Assistant (Rule 1067) | Altered concepts identified | Mon 4/27/09 11:00:34 PM | ↻ Approve  ⊗ Reject  ⓘ View Details |

FIG. 8

| | A | B | C |
|---|---|---|---|
| 3 | Receive Starting Email | No | Used to indicate if an email should be sent to the owner when the processing of his/her file starts. (No longer use) |
| 4 | Receive Completed Email | Yes | Used to indicate if an email should be sent to the owner when the processing of his/her file is complete. (No large use) |
| 5 | Match Staging Sheet | Matching Stage | Name of the sheet that contains the matching input. |
| 6 | Match HDD Results Sheet | Matching HDD Results | Name of the sheet that contains the matching results from CDR DEV. |
| 7 | Match KTMI Results Sheet | Match KTMI Results | Name of the sheet that contains the matching results from KTMIUA. |
| 8 | Stop Word Sheet | Stop Words | Name of the sheet containing the global stop word list. |
| 9 | Special Characters Sheet | Special Characters | Name of the sheet containing the global special charters. |
| 10 | Mapping Sheet | Stage Mappings | Name of the sheet containing references to the names of column headers used by BatchMatch. |
| 11 | Global Domain Inclusions | | List of comma-separated domains that the search should be limited to. |
| 12 | Global Domain Exclusions | | List of comma-separated domains that the search should not look in. |
| 13 | Global Context Inclusions | | List of comma-separated context NCIDs that the search should be limited to. |
| 14 | Global Context Exclusions | | List of comma-separated context NCIDs that the search should not look in |
| 15 | Normalizer | Base Normalizer | A normalizer is used to filter source and target strings by removing special characters, replacing stop words, performing stemming, etc. [BaseNormalizer] |
| 16 | Characters Limit | 2 | Set the character size of the words should be removed. (No longer use) |
| 17 | Matching Method | Dice | The match method is used to determine how similar two input strings are to each other, resulting in a percentage [Dice, WeightedDice] |
| 18 | Match Percentage | 90 | The percent limit that will be included in the match results, leave empty if all results should be returned. |
| 19 | Keywords Match Percentage | 60 | The percent limit for search where the Keyword(s) are Provided, leave empty if all results should be returned. |
| 20 | Match Selection Maximum | 1000 | The maximum size of the returning candidates for matching, leave empty if all results should be returned. |

FIG. 9

SYSTEMS, METHODS, AND APPARATUS FOR AUTOMATED MAPPING AND INTEGRATED WORKFLOW OF A CONTROLLED MEDICAL VOCABULARY

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to building and maintaining medical vocabularies. In particular, the present invention relates to systems, methods, and apparatus for supplementing a controlled medical vocabulary with localized clinical content.

Medical text plays an important role in the delivery of healthcare. Using medical text, medical concepts and information can be exchanged using a variety of documents including progress notes, discharge summaries, prescriptions, procedure reports, etc. Medical terminology is voluminous, fragmented, and complex. Multiple standards bodies (e.g., Health Level Seven (HL7), World Health Organization (WHO), etc.) make contributions to categorizing and publishing medical vocabularies (e.g. Systematized Nomenclature of Human and Veterinary Medicine (SNOMED), International Classification of Diseases (ICD), Logical Observation Identifier Names and Codes (LOINC), etc.) across multiple healthcare domains (e.g., medical procedures, problem lists, laboratory, etc.). In developing clinical information systems, data collection can be driven via a controlled medical vocabulary (CMV) that spans multiple organizations and source terminologies. The CMV can be continuously updated and is able to grow and evolve with the growing list of codes and terms.

In many cases, mapping between terminologies has been accomplished for common terminologies that have overlapping information domains. These mappings are made available by government agencies, healthcare providers, and third party content providers. Most approaches to managing a CMV rely on mapping rules and use of human intervention of terminology engineers or medical coders to understand differences across source vocabularies, to rationalize the organization of data (via hierarchies and relationships), to identify differences in granularity, and to map between codes and synonyms where there is overlap. This process requires a large amount of manpower to maintain an updated vocabulary and is especially burdensome when implementing new systems in an established healthcare organization with an abundance of systems and proprietary codes and synonyms. Combined with internationalization and a desire to share data across healthcare organizations, the problem quickly becomes unmanageable. For this reason, many healthcare IT providers have created their own proprietary codes, relationships, terms, and picklists which remain unintegrated with our systems and terminologies.

BRIEF SUMMARY

Certain examples provide systems, methods, and apparatus to provide clinical terminology services. Certain examples provide a controlled medical vocabulary supplemented by local clinical content.

An example provides a computer-implemented method to provide clinical terminology services. The method includes accessing an initial controlled medical vocabulary including at least one external terminology via a vocabulary management server. The method also includes processing local clinical content including unstructured local clinical content provided via an importer framework. The method further includes analyzing and extracting the unstructured local clinical content using a text analyzer and extraction tool to generate one or more proposed terms. Additionally, the method includes identifying one or more synonyms for the one or more proposed terms and placing the one or more synonyms into a queue to be added to the controlled medical vocabulary. The method includes reviewing the one or more synonyms placed into the queue. The method additionally includes adding the one or more synonyms to the controlled medical vocabulary with placement and relationship based on analyzing and extracting unstructured local clinical content to automatically map between the at least one external terminology and the local clinical content to supplement the controlled medical vocabulary with the local clinical content and provide the controlled medical vocabulary to one or more vocabulary consumers.

An example provides a clinical terminology services system providing a controlled medical vocabulary. The system includes an importer framework accessing an initial controlled medical vocabulary including at least one external terminology. The system also includes a vocabulary management server including terminology modeler and mapper to process local clinical content represented by one or more clinical models including unstructured local clinical content. The terminology modeler and mapper include a text analyzer and extraction tool to extract and analyze the unstructured local clinical content using a text analyzer and extraction tool to generate one or more proposed terms. The vocabulary management server facilitates identifying one or more synonyms for the one or more proposed terms, placing the one or more synonyms into a queue to be added to the controlled medical vocabulary, and reviewing the one or more synonyms placed into the queue. The vocabulary management server adding the one or more synonyms to the controlled medical vocabulary with placement and relationship based on analyzing and extracting unstructured local clinical content to automatically map between the at least one external terminology and the local clinical content to supplement the controlled medical vocabulary with the local clinical content.

An example provides an article of manufacture including a computer readable storage medium and executable program instructions embodied in the computer readable storage medium that, when executed by a computer processor, cause the computer to implement a method to provide clinical terminology services. The method includes accessing an initial controlled medical vocabulary including at least one external terminology. The method also includes processing local clinical content including unstructured local clinical content. The method further includes analyzing and extracting the unstructured local clinical content using a text analyzer and extraction tool to generate one or more proposed terms. Additionally, the method includes identifying one or more synonyms for the one or more proposed terms and placing the one or more synonyms into a queue to be added to the controlled medical vocabulary. The method includes reviewing the one or more synonyms placed into the queue and adding the one or more synonyms to the controlled medical vocabulary with placement and relationship based on analyzing and extracting unstructured local clinical content to automatically map between the at least one external terminology and the local clinical content to supplement the controlled medical vocabulary with the local clinical content.

BRIEF DESCRIPTION OF SEVERAL VIEWS OF THE DRAWINGS

FIG. 8 depicts an example integrated message inbox providing messages and/or updates to facilitate a human workflow and/or an automated machine workflow.

FIG. 9 depicts an example template defining matching parameters.

Figure 1:
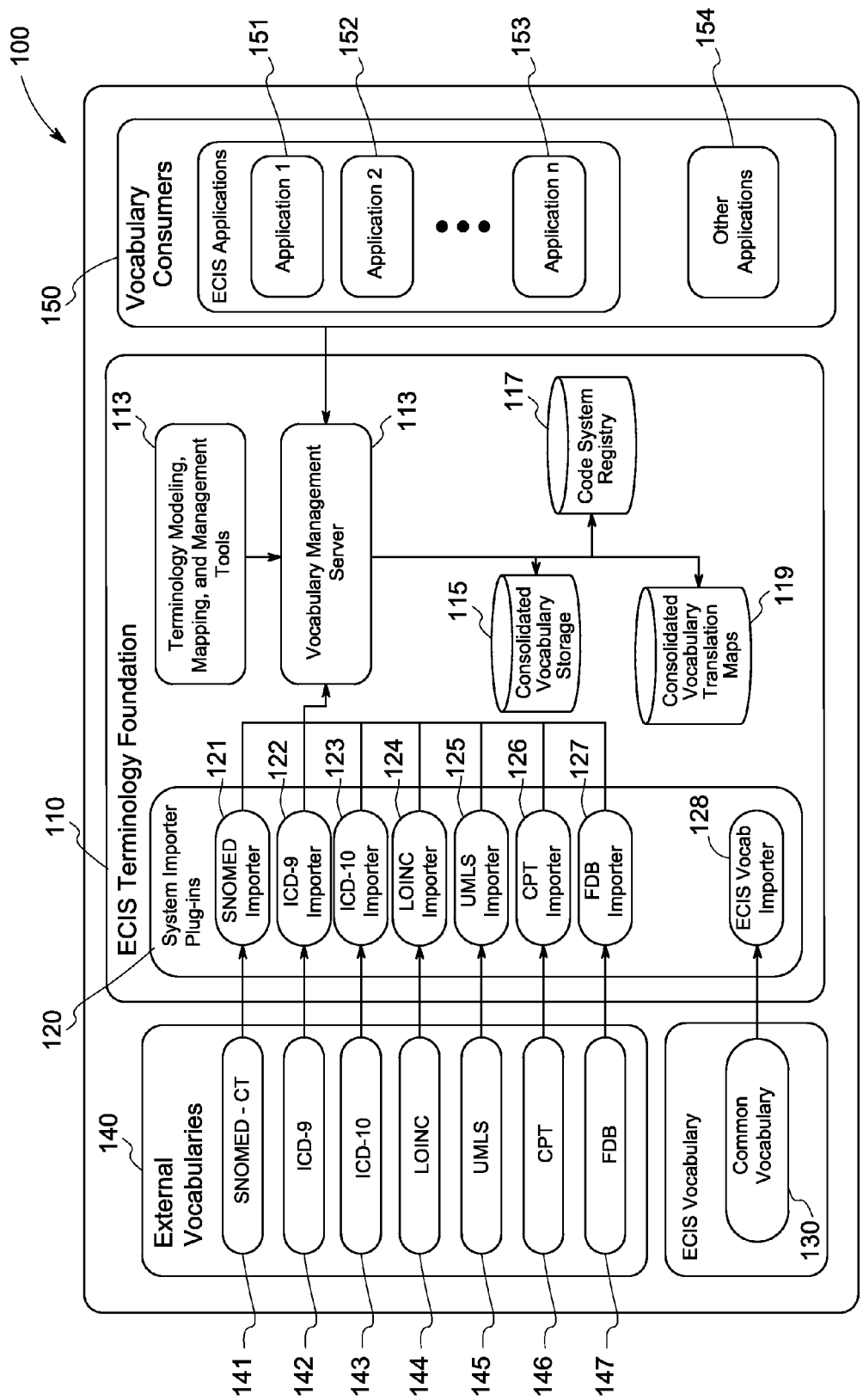
FIG. 1 illustrates an example controlled medical vocabulary (CMV) system.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, in an embodiment, at least one of the elements is hereby expressly defined to include a tangible medium such as a memory, DVD, CD, etc. storing the software and/or firmware.

A clinical system that is driven by standardized, coded data can help advance analytics, real-time decision support, and business intelligence for healthcare practitioners. In an example, an approach is provided for automating a mapping between external terminologies and use of text-based analysis to provide additional information and presentation of medical codes and terms by supplementing the data with localized clinical content from healthcare providers implementing the clinical system.

In an example, healthcare terminology provider data is analyzed using an algorithm that ranks criteria including the granularity of a medical term (e.g., simpler words have a smaller number of letters), the popularity of a term (e.g., how often is the term used by the organization), and the relationship to similar terms (informed by semantic proximity, other medical publications, and external dictionaries, for example). This analysis results in one or more proposals of where to place the provider's data and representations of data in a controlled medical vocabulary that spans organizations. Since the provider data is mapped to standards, interoperability and the use of localized terms are both possible.

Medical terminology vocabularies often include overlapping information. In an example, similarities and overlapping elements between vocabularies are identified. A confidence level of the similarity between the elements can then be provided. Rather than requiring a significant amount of human resources to review each term, often without regard to applicable standards, some review can be automated to reduce the amount of analysis left for manual human review.

In an example, a controlled medical vocabulary (CMV) is created for a clinical system and/or clinical application that covers a variety of terms (e.g., everything from problem lists to allergies to drugs). The terminology is transferred to an "inbox" with one or more proposed mappings using SNOMED, ICD9, ICD10, LOINC, Digital Imaging and Communications in Medicine (DICOM), American College of Radiology (ACR) Index of Radiological Diagnoses, American National Standards Institute (ANSI) identifiers, etc., and/or into a visual mapping tool where a user can see those mappings in more of a visual way to help a person developing a CMV.

A CMV is a capability of a computer-based patient record (CPR) system. Other CPR core capabilities include clinical documentation and data capture, clinical display including a clinical dashboard, a clinical workflow, order management including physician order entry, a clinical data repository (CDR), clinical decision support (CDS), privacy support, and interoperability connectivity. A CMV supports medically relevant concepts, terms, codes and relationships.

CMV services can be delivered using a vocabulary server that provides access to a set of CMV functions as a series of application programming interfaces (APIs). This approach makes the CMV accessible to any software component in the CPR or its environment that uses such services. In many cases, a set of terminologies such as SNOMED, ICD-9, ICD-10, and Current Procedural Terminology-Fourth Edition (CPT-4), including cross maps between their respective terms, is included. Using the CMV and vocabulary server, vocabulary services can be provided to subsystems of a core CPR system as well as other subsystems in the CPR environment. The CMV and vocabulary server can provide information concerning a medical term or concept to an executing application and can also accept terminology updates.

Using a CMV, CPR systems can understand and more intelligently process medical information while continuing to store that information in a form (e.g., medical terms) that permits humans to interact with the same data. In an example, a user may enter a query against information in a data warehouse (which has received its data from the CDR) asking to retrieve cases corresponding to certain search terms. If the CMV has been used to classify the information in the data warehouse, then the query should successfully retrieve all relevant cases including cases using equivalent terminology. The CMV can provide a comprehensive answer by using a search algorithm to explore its semantic network, for example.

In an example, limited CMV capabilities exist in a CPR system. For example, CMV capabilities allow mapping terms into canonical terms, generating billing codes, etc. These mappings can be hard-coded into applications, for example. In such environments, a CPR system supports generation of standard code sets such as ICD-9 and CPT-4.

In an example, the CMV exists as an architecturally separate component in the CPR. The CMV can be used to explicitly manage concepts, terms, and relationships, as well as cross-mapping these concepts, terms, and relationships to standardized encoding schemes. Applications such as clinical decision support and clinical workflow can have a significant degree of CMV interaction. An API for a vocabulary server supports the vocabulary needs of the clinical decision support and clinical workflow as well as related applications and/or components. The CMV/vocabulary server combination can support tools to enable terminologies to be updated and to resolve resulting conflicts. Proposed CMV content can be compared to current CMV content, establish semantic consistency in the new content, and track changes made to the CMV.

In an example, a vocabulary server supports interacting vocabulary needs of the CPR environment. The vocabulary server permits users to interactively explore the vocabulary's semantic network, maintain local vocabulary variations, incorporate new content, handle versioning issues, and provide real-time (or substantially real-time) responses to queries for vocabulary services. To support a full spectrum of CPR functions, the CMV provides "decompositional completeness". That is, the CMV contains atomic representations of pre-coordinated terms contained in the CMV. Thus, if the CMV includes a pre-coordinated term or phrase including multiple elements, then the CMV includes primitive terms for each of those elements. The CMV also includes a convention or rule that describes how to use the primitive terms for each of the elements to create a post-coordinated term having the identical semantic content as the pre-coordinated term. A CMV that provides decompositional completeness enables applications, such as medical natural language processing applications, to function properly despite the existence of pre-coordinated terms that differ in form from the specific terms that may be created by a CPR system user (e.g., "myocardial infarction" versus "heart attack"). The CMV can also support the clinical workflow and clinical decision support capabilities of the CPR system. CMV can be used to support evidence-based medicine (EBM) functions such as automated care guideline protocols. The CMV also includes support for manual vocabulary updates and resolution of vocabulary semantic conflicts.

In an example, the CMV and vocabulary server support a full range of real-time vocabulary services, as well as being able to receive automated updates from vocabulary authorities. The CMV supports many industry-standard coding systems. The vocabulary server management system supports automated integrity checking of the CMV's semantic network and can provide automated support for EBM functions. The CMV can be combined with capabilities such as clinical workflow, CDS, EBM, natural language processing, and continuous speech recognition to provide an environment where a variety of clinical input (e.g., typing, speech, menu picks, and external documents) are incorporated into the CPR system's functions. The CMV can work in conjunction with clinical workflow and CDS to help provide knowledge management within the CPR system.

In an example, a mapping between external terminologies and use of text-based analysis to provide additional meaning and presentations of medical codes and terms by supplementing the data with localized clinical content is automated. The example process can include the following: 1) An initial CMV is created by cloning sections of external terminologies based on healthcare data domain (e.g., LOINC for laboratory terminology, CPT for medical procedures, etc). The structures (e.g., relationships, concepts, and terms) of the standard terminologies are retained where applicable. Mappings between the CMV and publicly available mappings (e.g., ICD-9 to ICD-10, SNOMED to CPT, etc.) are then used to create a web of related data. The web of data includes both direct (e.g., equivalent) and indirect mappings (e.g., is broader than, is narrower than). 2) Rules are created based on the mappings to determine how to handle changes to the source terminology. For example, when a new term is added by a third party organization, then the mapping for sister terms may specify to automatically propagate 'additions' or put them into proposed status for review. 3) In addition to creating a CMV based on standard vocabularies, customer presentations and mappings can also be included. To create such a CMV, a healthcare organization aggregates its clinical content including nursing, physician, and administrative documents, for example. Much of this data is currently collected in an unstructured mechanism via comment and note fields and thus very difficult to maintain in a structured terminology system. 4) This unstructured clinical content is then run through a text analyzer and extraction tool to organize the information based on synonyms, abbreviations, and relevance to existing source terminologies, for example. 5) Source terminologies and medical dictionaries are used to augment the intelligence of the text analyzer. 6) Proposed terms and synonyms are extracted based on linguistic and probabilistic algorithms. Proposals are put into a queue for a terminology engineer to validate and promote to the controlled medical vocabulary, for example. 7) Local synonyms and presentations based on the unstructured data analysis can be automatically put into a proposed queue to be added to the CMV.

In an example, controlled medical terminology services and modeling and management tools are used to provide advanced analytics, real-time decision support, and business intelligence through use of structured, coded data. CMV systems store high quality, computationally comparable, reliable, and reusable data to support such services. Additionally, internal and external interoperability of systems, processes, and data can be provided to reduce costs incurred due to redundant and disparate data definition, storage, and maintenance and to promote national and international interoperability by sharing terminology with the healthcare community at large, for example.

As shown in FIG. 1, for example, a controlled medical vocabulary (CMV) system 100 includes a terminology foundation subsystem 110, a common vocabulary 130, one or more external vocabularies 140, and one or more vocabulary consumers 150.

The terminology foundation subsystem 110 includes modeling and management tools and common terminology services for code mapping, browsing, and querying services. For example, the terminology foundation subsystem 110 includes terminology modeling, mapping, and management tools 111, a vocabulary management server 113, a consolidated vocabulary storage 115, a code system registry 117, and consolidated vocabulary translation maps 119. The terminology foundation subsystem 110 also includes one or more system importer plug-ins 120. The system importer plug-ins 120 can include one or more of a SNOMED importer 121, an ICD-9 importer 122, an ICD-10 importer 123, a LOINC importer 124, a Unified Medical Language System (UMLS) importer 125, a CPT importer 126, a First Data Bank (FDB) importer 127, and a common vocabulary importer 128.

External vocabulary(ies) 140 can include a SNOMED-CT vocabulary 141, an ICD-9 vocabulary 142, and ICD-10 vocabulary 143, a LOINC vocabulary 144, a UMLS vocabulary 145, a CPT vocabulary 146, an FDB vocabulary 147, etc.

Vocabulary consumer(s) 150 can include one or more applications 151-154. Vocabulary consumers 150 communicate with the terminology foundation subsystem 110 using technology services, such as HL7 Common Technology Services (CTS) 160.

Using the system importer 120 of the terminology foundation subsystem 110, external code systems (e.g., SNOMED, LOINC, CPT, ICD-9, ICD-10, etc.) can be loaded into a consolidated repository. Modeling tools 111 allow informaticists to create, modify, map, and/or manage vocabulary concepts. Data storage and services 113 are used to store and retrieve external code systems 117, translation maps 119, and a controlled medical vocabulary 115. Browsing, code mapping, and runtime services based on the HL7's Common Terminology Services 160 specification support a standards-based controlled medical vocabulary. Versioning, life cycle management, dependency resolution, and packaging services support publishing of terminology across environments.

Figure 2:
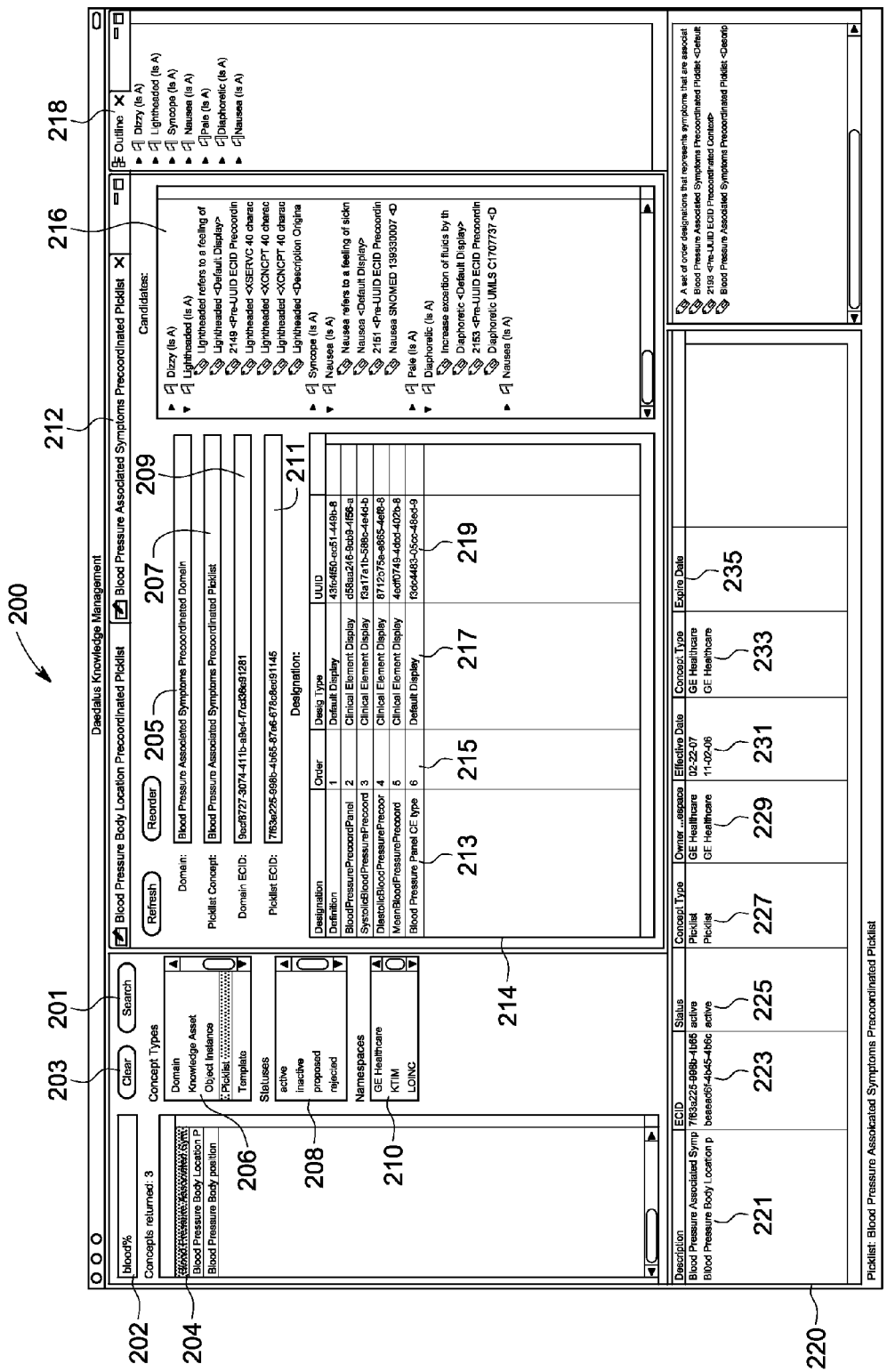
FIG. 2 illustrates an example terminology mapping tool interface.

As illustrated, for example, in FIG. 2, terminology mapping tools load controlled vocabulary content (e.g., LOINC, SNOMED, ICD-10, etc.) from standards organizations and allow informaticists to create, modify, map, and/or manage vocabulary concepts. Using a knowledge management interface 200, shown, for example, in FIG. 2, a search input 202 returns one or more resulting vocabulary concepts 204. The search input 202 can be executed or cleared using buttons 201, 203, respectively. Search results 204 can be filtered and/or sorted by one or more additional criteria such as concept type 206, status 208, namespace/owner 210, etc. Selecting a concept in the search results 204 displays information regarding that concept in a display area such as the picklist 212 shown in FIG. 2. Within the picklist 212, information relating to the selected concept 204, such as domain 205, picklist concept 207, domain enterprise concept identifier (ECID) 209, and picklist ECID 211, is displayed for user review, input, and/or modification. Designations 214 within the selected concept 204 are provided, including designation name 213, order 215, type 217, and universally unique identifier (UUID) 219, for example. Additionally, one or more candidate symptoms 216 are provided including detail regarding each symptom. These symptoms are also displayed in an outline 218.

A set of selected concepts 220 is also provided at the bottom of the interface 200. The set 220 summarizes the description 221, ECID 223, status 225, concept type 227, owner/namespace 229, effective date 231, concept type 233, and expiration date 235 for each concept. The interface 200 also provides notes 222 regarding a selected concept.

For example, as depicted in the interface 200 of FIG. 2, a user can search 202 for vocabulary concept(s) involving words starting with "blood." A user can select a concept type 206, such as a picklist, a status 208, such as active, and a namespace 210, such as GE Healthcare, to refine the search results. A returned concept 204 can be selected to populate the domain 205, picklist concept 207, domain ECID 209, and picklist ECID 211, for example. For the selected concept picklist, designation information 214 including designation name 213 (e.g., blood pressure panel), order number 215 (e.g., 1 through 6), designation type 217 (e.g., clinical element display, default display, etc.), and UUID 219 can be provided. One or more candidate symptoms 216, such as dizziness, lightheadedness, nausea, etc., can be selected and also provided in outline 218 form. A set 220 of selected concepts 204, such as one or more blood pressure concepts, provides a summary of ECID 223, status 225, concept type 227, owner/namespace 229, effective date 231, concept type 233, and/or expiration date 235.

Concepts from a controlled terminology may not be sufficiently meaningful without a clinical structure to provide context. With a large number of equally correct ways to say the same thing, understanding a desired meaning becomes unreasonably burdensome. Clinical Element Models (CEMs) can be utilized as the basis to model, store, and/or retrieve dynamically changing clinical concepts and information.

A CEM is a data structure that represents a unit of medical information, including its interrelated components. CEMs enable content-driven systems development so that healthcare delivery can be documented consistently, measured reliably, and improved continuously over time and across patients, providers, care settings, and applications.

Figure 3:
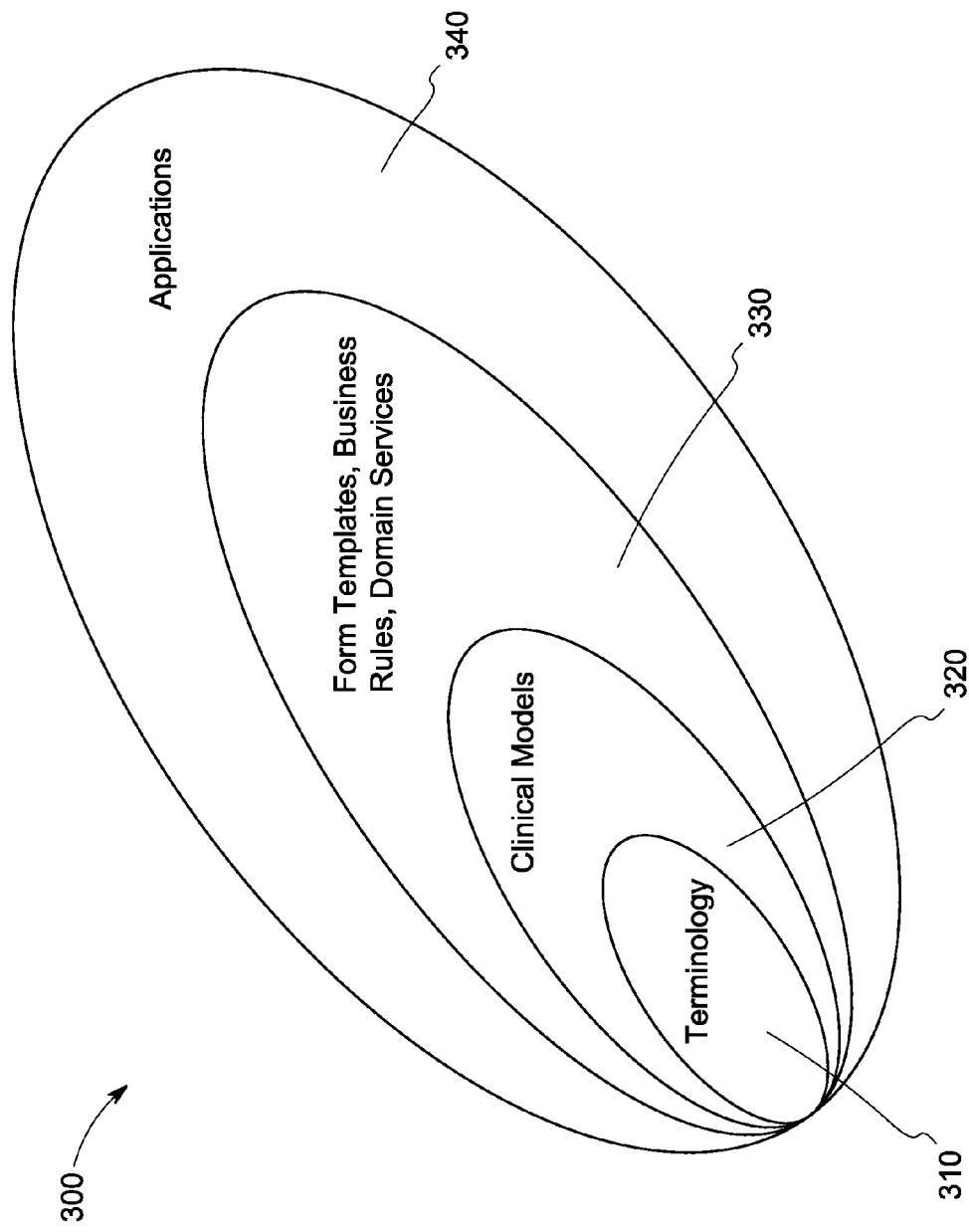
FIG. 3 illustrates an example coded, controlled medical vocabulary that can serve as a basis for understanding clinical data.

A controlled medical vocabulary and clinical models form the basis for a content driven system that supports dynamic data, workflows, and/or decision support. As illustrated, for example, in FIG. 3, a terminology 310 provides a coded, controlled medical vocabulary that can serve as a basis for understanding clinical data. One or more clinical models 320 provide detailed clinical element models (CEMs) representing information models bound to the terminology 310. One or more form templates, business rules, and/or domain services 330 provide reusable elements that add context regarding how an application would utilize content. The form templates, business rules, and/or domain services 330 are consumers of the clinical models 320 and terminology 310. One or more applications 340 provide content-driven applications whose behavior is driven by dynamic templates and rules based on the form templates, rules, and/or services 330, clinical models 320, and terminology 310.

As used herein, several components provide information and functionality for terminology management. Example definitions of these components are provided below.

A code system is a resource that makes assertions about a collection of concepts, where the concepts are uniquely identified by concept identifiers and represented by designations. Code systems are often referred to as terminologies, vocabularies, coding schemes, and/or code sets. A code system can be a terminology (e.g., LOINC), a vocabulary (e.g., SNOMED), a classification (e.g., ICD-9 CM), a thesaurus (e.g., MeSH), an ontology (e.g., FMA), or just a list of codes (e.g., HL7 code systems). A code system may include concept relations where concepts are related by certain relationships, or a code system may just contain a flat list of codes with their designations, for example. A given code resolves to one meaning within the code system.

A concept is description of a unit of knowledge created by a combination of concept properties and concept relations within the context of a code system. A concept identifier is a numeric or alphabetic symbol that identifies a concept within the context of a code system. A concept identifier is often referred to as an entryCode (e.g., in Mayo Clinic's Lexical Grid or LexGrid framework for representing, storing, and querying biomedical terminologies) and concept code (e.g., in HL7, CTS II), or just a code. The concept identifier can be meaningful when it is related to the concept properties of the concept, such as mnemonic codes, hierarchical codes, etc. The concept identifier can be non-meaningful when it is not related the concept properties, such as sequential id, UUID, etc.

A qualified concept code is a combination of a code system identifier and a concept identifier. A qualified concept code provides a globally unique name for the description and, by proxy, the referenced "unit of knowledge". HL7 uses ISO Object Identifiers (OIDs) as code system identifiers. LexGrid uses Universal Resource Identifiers (URIs). The current KTMI system uses DCE UUIDs for both code system identifiers and locally authored concept identifiers. Note that both OIDs and UUIDs can be transformed into URI's by prefixing them with "urn:oid:" and "urn:uuid:" respectively.

A concept property is an abstraction of a characteristic of a concept for defining and identifying the concept. A designation is a textual concept property that can be used to represent the intended meaning of a concept in certain usage context. A designation is often referred to as presentation (LexGrid), representation, term (ISO 17115), name (HL7), etc. A definition is a concept property that provides a textual definition of the concept.

A relationship type is a binary predicate that, when asserted to be true between two concepts, asserts that a corresponding external relationship applies between the classes and/or instances described by the concepts. A relationship type is referred to as an association in LexGrid, although the LexGrid model confuses the type (association as entity) and the set of assertions (association container for association-Source).

A relationship is an assertion of an association that pertains between two or more concepts through hierarchical, associative, sequential, temporal or causal relationship types. Concept relation is often referred to as association (e.g., LexGrid), relation, concept relationship (e.g., CTS II), relationship, hierarchy. Association in LexGrid allows the source and target concepts to be from different code systems.

A usage context is a set of conditions that need to be fulfilled before a terminological component (includes concept property, designation, relationship, picklist, concept map) is eligible for usage. Usage context is often referred to as context of use, context, and/or application context. Usage context includes application contexts, clinical contexts, user contexts, patient contexts, etc. The set of conditions can be pre-coordinated into a description of an environment, or stays as multi-parameter conditions. The HL7 usage context is limited to the conditions in which a Value Set (See Value Set section) may be used.

A picklist is an ordered list of designations where the concepts represented by the designations are drawn from the same value set. Since the value sets in LexGrid, HL7 and CTS II are independent of specific code system, a picklist can also be generated with values from multiple code systems, for example.

A concept map is a set of rules for transforming a concept from one code system to a concept in another code system. A concept map is often referred to as concept mapping, or just mapping, association (e.g., LexGrid).

A value set definition is a set of rules that, when applied to a code system version, results in a list of qualified concept codes. A value set definition may represented by a simple list of one or more concept codes or by a formula such as "all concept codes in a specific namespace", "all concept codes that are the target or source of a concept relationship", "all concept codes referenced by another value domain definition", etc.

A value set is a combination of a set of qualified concept codes resolved from value set definition and the corresponding values that represent the qualified concept codes in the context of a specific message or database. Value sets are frequently created algorithmically. Common value set algorithms include the specification that the concept identifier will represent the qualified concept code, that the preferred designation will represent the qualified concept, and/or that the value of a particular property will represent the value, for example.

Figure 4:
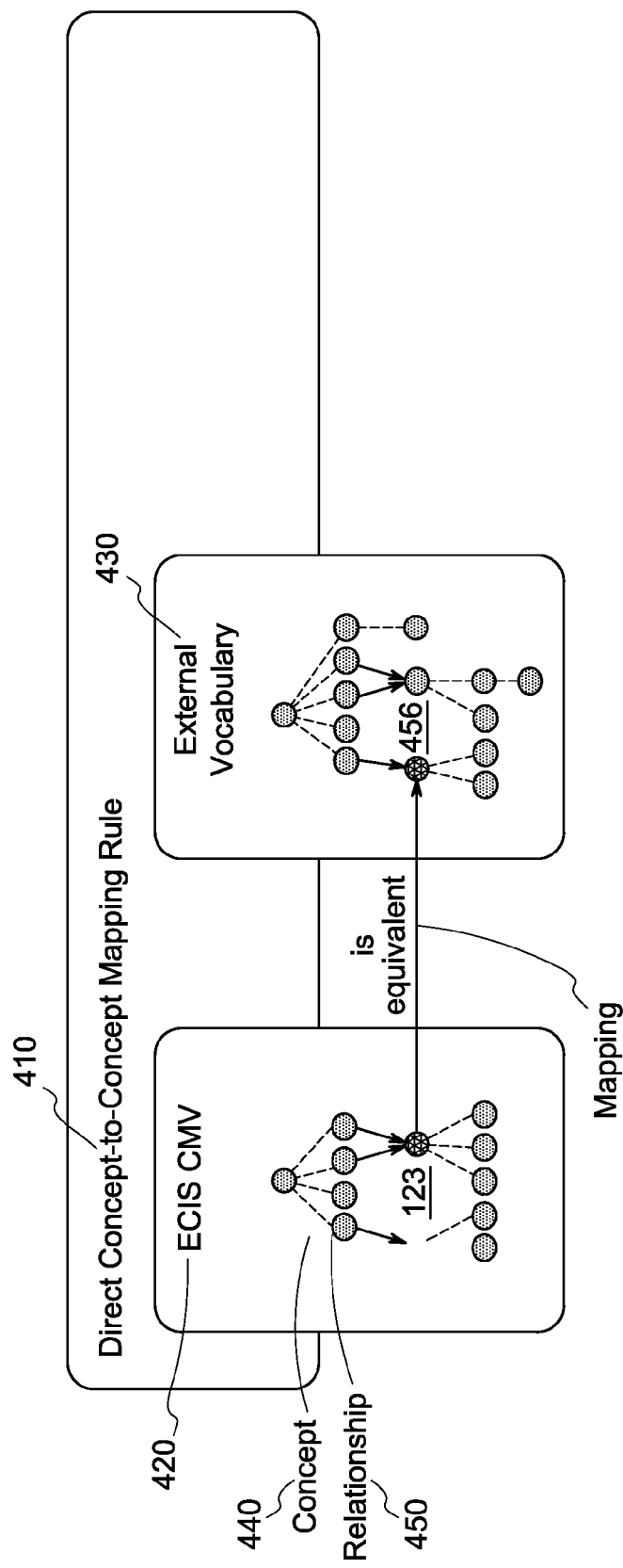
FIG. 4 depicts an example direct concept-to-concept mapping rule applied between a clinical information system CMV and an external vocabulary.

In an example, concepts are automatically mapped. For example, as depicted in FIG. 4, a direct concept-to-concept mapping rule 410 can be applied between a clinical information system CMV 420 (e.g., GE Enterprise Clinical Information System (ECIS) controlled medical vocabulary) and an external vocabulary 430 (e.g., RxNorm, SnomedCT, LOINC, ICD-9, etc.). In the example of FIG. 4, a concept 123 is equivalent to a concept 456. As illustrated in the example of FIG. 4, each concept can be related to one or more concepts 440 by relationships 450. Since the concept 123 is automatically identified as equivalent to the concept 456, by rule, changes to concept 456 in subsequent versions of the external vocabulary 430 are identified and automatically proposed in the CIS CMV 420.

Figure 5:
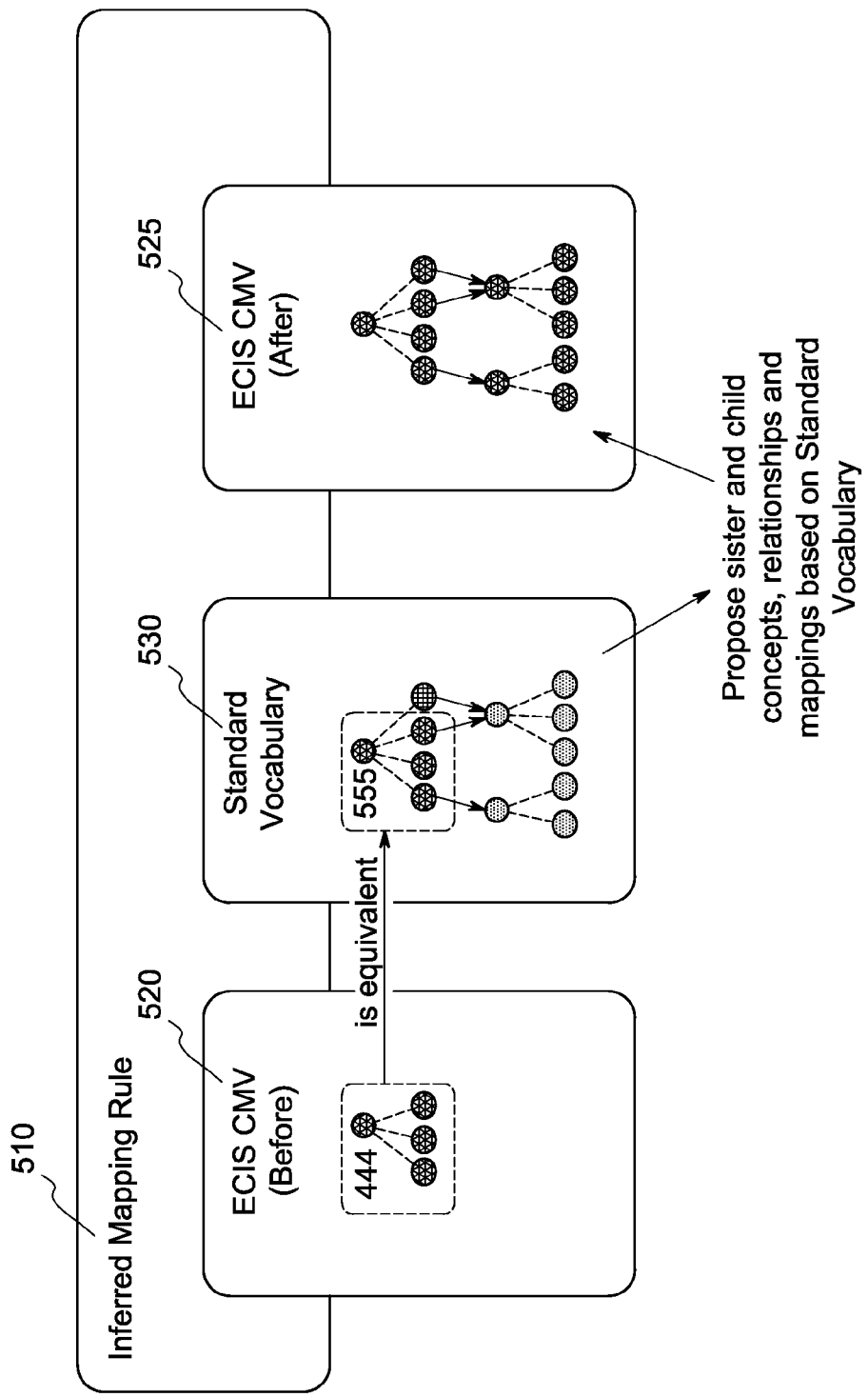
FIG. 5 depicts an example inferred mapping applied to a CMV and a standard vocabulary to generate an updated, inferred CMV mapping.

Alternatively and/or in addition, an inferred mapping rule can be applied to concepts. As illustrated, for example, in FIG. 5, an inferred mapping 510 is applied to an ECIS CMV 520 and a standard vocabulary 530 to generate an updated, inferred ECIS CMV mapping 525. In the example of FIG. 5, a concept 444 is equivalent to a concept 555. Using the inferred mapping rule 510, sister and child concepts, relationships, and mappings are proposed based on the standard vocabulary 530. By rule 510, sister and child concepts in the ECIS CMV 520, 525 are automatically proposed based on the standard vocabulary 530.

Figure 6:
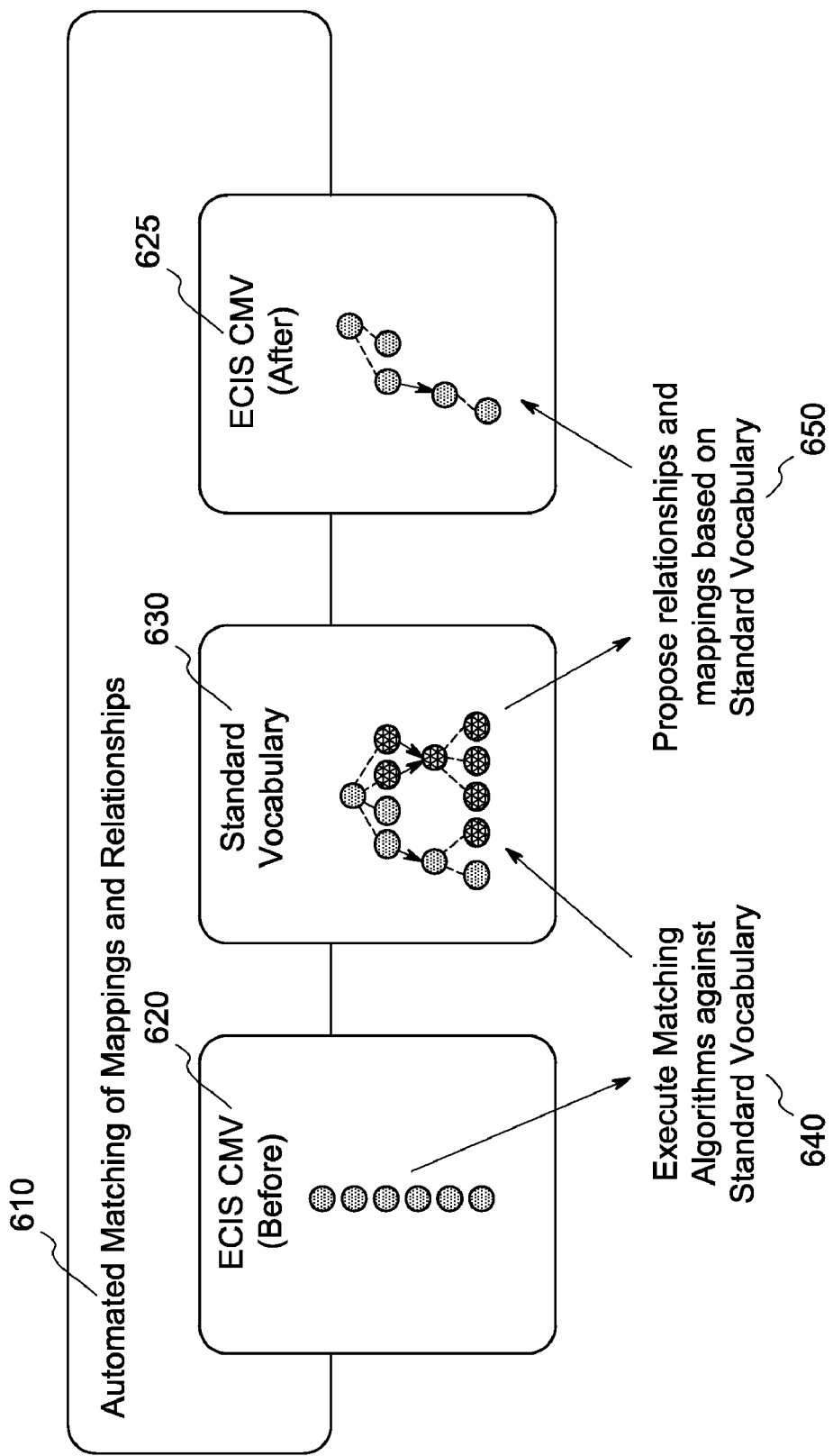
FIG. 6 depicts an example automated matching of mapping and relationships applied to a CMV and a standard vocabulary to generate an updated CMV mapping.

As illustrated in example FIG. 6, relationships between concepts can be inferred. Using an automated matching of mappings and relationships 610, an ECIS CMV 620 and a standard vocabulary 630 can generate an updated ECIS CMV 625. Matching algorithms 640 can be applied to the ECIS CMV 620 based on the standard vocabulary 630. Then relationships and mappings for the updated CMV 625 can be proposed 650 based on the standard vocabulary 630.

Figure 7:
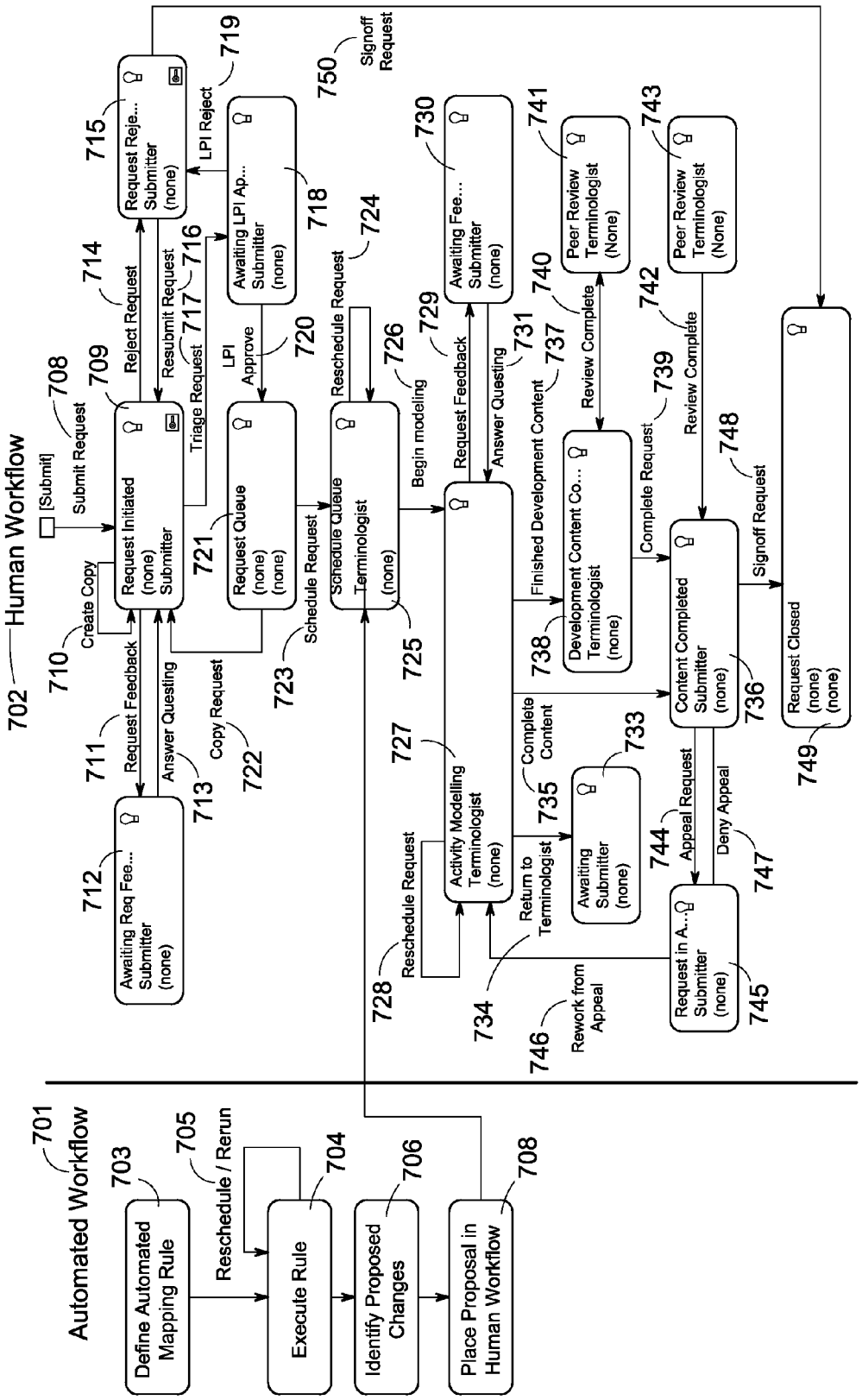
FIG. 7 illustrates an example integrated workflow combining automated and human workflows for terminology modification workflow development and execution.

FIG. 7 illustrates an integrated workflow 700 combining automated and human workflows 701, 702 for terminology modification workflow development and execution. At 703, an automated mapping rule is defined. For example, an automated mapping rule for concepts based on relationships can be defined. At 704, the rule is executed. At 705, rule execution can be rescheduled and/or rerun if applicable. At 706, proposed change(s) to the mapping are identified. At 707, one or more proposed changes are placed in the human workflow 702. The proposal is deposited in a scheduled queue 725 for a particular terminologist and/or type/group of terminologist.

Alternatively or in addition, a terminology request can be submitted at 708 for terminologist review. At 709, the request is initiated. At 710, a copy is created and, at 711, feedback is requested. At 712, the request is queued to await feedback. When a reviewer provides feedback, the answer is provided at 713. At 714, a rejected terminology request is provided to a rejected request queue 715, where the request can be resubmitted 716 or signed off 750.

At 717, a request can be triaged and sent to a quality assurance representative for approval 718. If the quality assurance representative rejects the request 719, then the request is routed to the rejected request queue 715. If the quality assurance representative approves the request 720, the request is submitted to a request queue 721. A copy of the approved request 722 can be sent back to the initiated request queue 709, for example. The request is then scheduled 723 in the scheduled queue 725 along with proposed mappings from the automated workflow 701. If applicable, a scheduled request can e rescheduled 724 based on terminologist and/or other resource availability, for example.

A request is taken from the scheduled queue 725 and modeling begins 726. The request being modeled is placed in an actively modeling queue 727. The modeled request can be rescheduled 728 in the actively modeling queue 727. During modeling, feedback can be requested 729. The request awaits feedback in a feedback request queue 730, and an answer is returned 731 to the actively modeling queue 727. At 732, the modeled request is submitted for approval. After waiting for approval 733, the request is returned to the terminologist 734. At 735, content is completed and placed in a content completed queue 736.

Alternatively, at 737, development content is finished in the development content completion queue 738. After development content is finished, a complete request 739 is sent to the content completed queue 736. A peer review 741 can be requested and review results 740 communicated for the development content 738.

Similarly, content in the content completed queue 736 can be peer reviewed 743 with review results provided 742. A request can also be appealed 744. Appeals requests 745 are reviewed. If a request for appeal is granted 746, modeling 727 is reworked from the appeal. If a request for appeal is denied 747, then the submitter is notified at the content completed queue 736. At 748, a request is signed off. At 749, a request is closed.

As depicted, for example, in FIG. 8, an integrated message inbox 800 provides messages and/or updates to facilitate both a human workflow 810 and an automated machine workflow 820. For example, the terminology management 810 includes a plurality of messages 830-834 and provides information and action functionality regarding each of the messages 830-834 including a sender 840, a subject 842, a received date/time 844, and an action 846. An executable action 846 can include approve 850, reject 852, and/or view details 854, for example.

As shown, for example, in FIG. 9, matching parameters can be defined via one or more templates 900. Using the template 900, one or more parameters 910 can be assigned a value 920 for use in terminology services, for example. For example, parameters 910 such as matching states, matching results, stop words, special characters, stage mappings, exclusions, inclusions, limits, match percentages, match selection maximum, matching method, etc. can be specified with a value 920, as shown, for example, in FIG. 9. Additionally, an explanation 930 can be provided to explain the parameter 910 and/or provide guidance as to specifying a value 920 for the parameter 910, for example.

Figure 10:
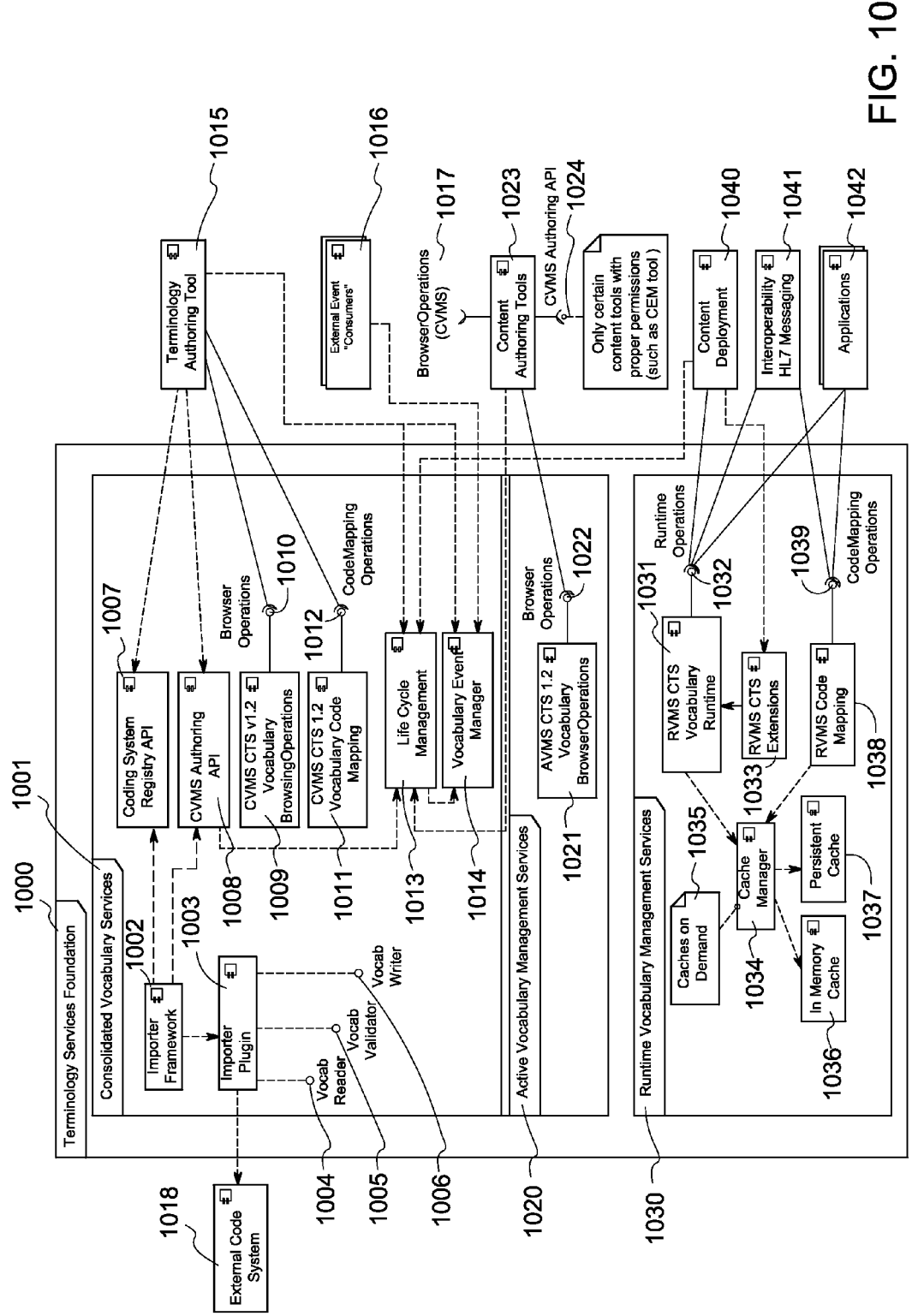
FIG. 10 illustrates an example high level component diagram of a Terminology Services Foundation.

FIG. 10 illustrates an example high level component diagram of a Terminology Services Foundation 1000. The Terminology Services Foundation 1000 can be logically divided into three areas: Consolidated Vocabulary Management (CVM) 1001, Active Vocabulary Management (AVM) 1020, and Runtime Vocabulary Management (RVM) 1030. These modules or subsystems can be defined as logical distinctions and/or as physical components within the system. Each area communicates the responsibilities of the Terminology Services Foundation 1000.

Briefly, CVM services (CVMS) 1001 is responsible for storage of and access to internally and externally (imported) authored terminology data. The AVM services (AVMS) 1020 is responsible for the storage of and access to vocabulary actually used in the clinical information system product. This provides decoupling from external code systems, installation management, maintenance, and performance optimizations, for example. The RVM services (RVMS) 1030 is responsible for acting as a cache layer on top of the AVMS 1020 in order to provide performance enhancement for runtime applications, for example.

Common Terminology Services (CTS) provide a common set of terminology or vocabulary services such as those defined by the HL7 healthcare standards body. The HL7 CTS specification, for example, includes detailed requirements and design for a CTS implementation. Vocabulary services can be further divided into two sections: Runtime and Browser operations. Runtime operations are services for performance of dynamic vocabulary lookup. Browser operations are designed for browsing and searching use cases.

Consolidated Vocabulary Management Services (CVMS) 1001 permits authoring, browsing, and interaction with all of the terminology authored by terminology engineers, along with importing and browsing other reference terminologies such as SNOMED CT. The CVMS 1001 also contains mappings between terminologies. Mappings can include mapping ECIS concepts (e.g., the ECIS Code System) to external terminologies if the ECIS concepts were created from external terminologies. However, the CVMS 1001 can permit mappings between any two terminologies, including those that are not created or maintained internally. For example, the system represents mapping between an internally created procedure concept derived from CPT and the CPT concept from which the concept originated. If a mapping exists between the CPT concept and a related SNOMED-CT concept, the system can represent and provide information about that mapping.

The ECIS Code System includes the concepts to be used in the ECIS system. These concepts include those created by the authoring features of the CVMS 1001 and those cloned from external vocabularies. Cloning concepts from external vocabularies provides a layer of protection from changes to the external vocabularies allowing terminology engineers the ability to control and otherwise maintain the system's medical vocabulary.

In an example, the CVMS 1001 includes both terminology intended for ECIS and reference terminologies. In an example, ECIS terminology is distinct from the reference terminologies to allow external applications to access the reference terminologies. Some applications, such as billing and data warehousing, may require access to complete sets of reference terminology that do not have ECIS terms associated with them to support reporting, analysis, and other functionality, for example. In an example, a logical "wall" can be formed between the Active Terminology store and the Consolidated Terminology store. The wall helps to restrict access since authoring terminology, which are all the concept versions in the consolidated store that have not been activated and have been created by the authoring tools rather than imported into the CVMS 1001 as external vocabularies, should be inaccessible from running applications for controlled terminology maintenance, staging, and development, for example. Alternatively or additionally, a system design permits application access to the reference terminologies for a fully featured system. In an example, the two terminology sets can exist in the same logical instance or be logically separated, with authoring terminology isolated from access while the reference terminologies are externally accessible.

In an example, the system permits loading of external terminologies through a defined import process. These imports can be handled through separate importers, for example, sharing the same core functionality with customization for each terminology handled through a configurable extension layer. This layer can be specified in some configuration format, such as XML, permitting adjustments as the external terminology representation evolves. This evolution of format may happen more frequently than expected in terminologies, usually with early notification from the terminology provider. Where possible, such an importer can connect to an external feed from a file transfer protocol/hypertext transfer protocol (FTP/HTTP) provider as its input. Additionally, auto-scheduling can be provided for such import jobs, for example.

In an example, CVMS 1001 supports various authoring metadata for internal authoring purposes and/or for external vocabularies that are in flux. This includes an overall status of a concept in its lifecycle (e.g., whether the concept is newly proposed, in process, awaiting review, rejected, approved for usage, etc.). Additionally, CVMS 1001 includes auditing information indicating when concepts were moved from the system into the Active Terminology system. Two example models are described for moving data from CVMS 1001 to the Active Terminology Storage. The first example model is a temporal-delta model, where any change from a previous version in the correct status is moved to Active Terminology when its publishing metadata is within a defined date range. The second example model is a manufacturing model, where content is given a target "drop" version, and where those concepts and changes in the desired version are bundled and moved together as a single job. For a model used, CVMS 1001 can represent the appropriate metadata and either provide services for pushing data to Active Terminology according to temporal-delta rules, or provide packaging and export services for manufacturing-style drops. In either case, CVMS 1001 can provide validation and metric reporting on data movement between systems.

In an example, CVMS 1001 can provide a repository storage scheme for registering which applications and peripheral individuals and systems are using a concept. Thus, a content element from the AVMS 1020 can register its usage of a concept to enable automated notifications as the concept evolves from version to version. The services can allow for both the registering and deregistering of applications and other "concerns," as well as specifying the level of alerts desired by the subscriber, for example. Such a concept registry involves an event framework for the notifications, and calls in response to changes of content and movement of data from CVMS 1001 to AVMS 1020, for example. This event framework can also be used to integrate CVMS 1001 with a content workflow system employed by requesters and fulfillers of terminology projects. That is, the event framework enables the automated progression of terminology workflow elements from state to state, firing the element's appropriate transition through web services, for example.

As shown in FIG. 10, the CVMS 1001 includes an importer framework 1002 and an importer plug-in 1003 to import terminology/vocabulary. The importer plug-in 1003 is connected to a vocabulary reader 1004, a vocabulary validator 1005, and a vocabulary writer 1006 which act upon the imported vocabulary. The importer plug-in 1003 provides information to an external code system 1018. The importer framework communicates with a coding system registry API 1007 and a CVMS authoring API 1008, which communicates with life cycle management 1013. The life cycle manager 1013 interacts with a vocabulary event manager 1014 to coordinate vocabulary lifecycle. The life cycle management 1013 and vocabulary event manager 1014 receive input from a terminology authoring tool 1015, one or more external event "consumers" 1016, content authoring tools 1023, and/or content deployment 1040, for example. The terminology authoring tool 1015 transmits information to the coding system registry API 1007 and the CMVS authoring API 1008. The terminology authoring tool 1015 also interacts with a CVMS CTS vocabulary browsing operations 1009 via browser operations 1010 and with a CVMS CTS vocabulary code mapping 1011 via code mapping operations 1012.

Active Vocabulary refers to a portion of all the vocabulary data from authoring (whether created or cloned from external vocabularies) that has been selected for use in the ECIS system. Vocabulary becomes part of the Active Vocabulary Management Services (AVMS) 1020 when the Life Cycle Manager moves it into the Active space, making it available for use by the runtime system. The AVMS 1020 data store may or may not be the same as the CVMS 1001 data store. Boundaries between the data stores can be logical and/or physical, for example.

Active Vocabulary services include, for example, implementations of HL7 Common Terminology Services 1.2 (CTS) for Browsing (AVMS CTS vocabulary browser operations 1021 and browser operations 1022 interacting with content authoring tools 1023) and potentially an API for more advanced querying (e.g., a CVMS authoring API accessible by certain content tools having proper permissions, such as a clinical element model (CEM) tool). When terminology is moved for the first time (e.g., first version Activated) from the CVMS 1001 to the AVMS 1020, the ECIS globally unique identifier (ECID) is created, if it does not already exist. When new version(s) of the same terminology entities are moved to the AVMS 1020 (e.g., an update), the same ECIDs will be used. The ECID follows a format that is globally unique, for example. In an example, an "abstract" ECID identifies all versions of a concept, and "precise" ECIDs identify each version individually—such that services can default to the latest version when given the abstract ECID, and that services can retrieve the precise version of a concept when given the precise ECID.

In an example, "authoring vocabulary" is not in the AVMS 1020. The AVMS 1020 includes the portion of the ECIS code system that has been activated at least once. The portion of the code system is the part of the ECIS code system that has been released for production use in the system. The CVMS 1001 has the imported code systems and the work-in-progress ECIS code system. "Authoring vocabulary" refers to the work-in-progress ECIS code system, for example.

Figure 11:
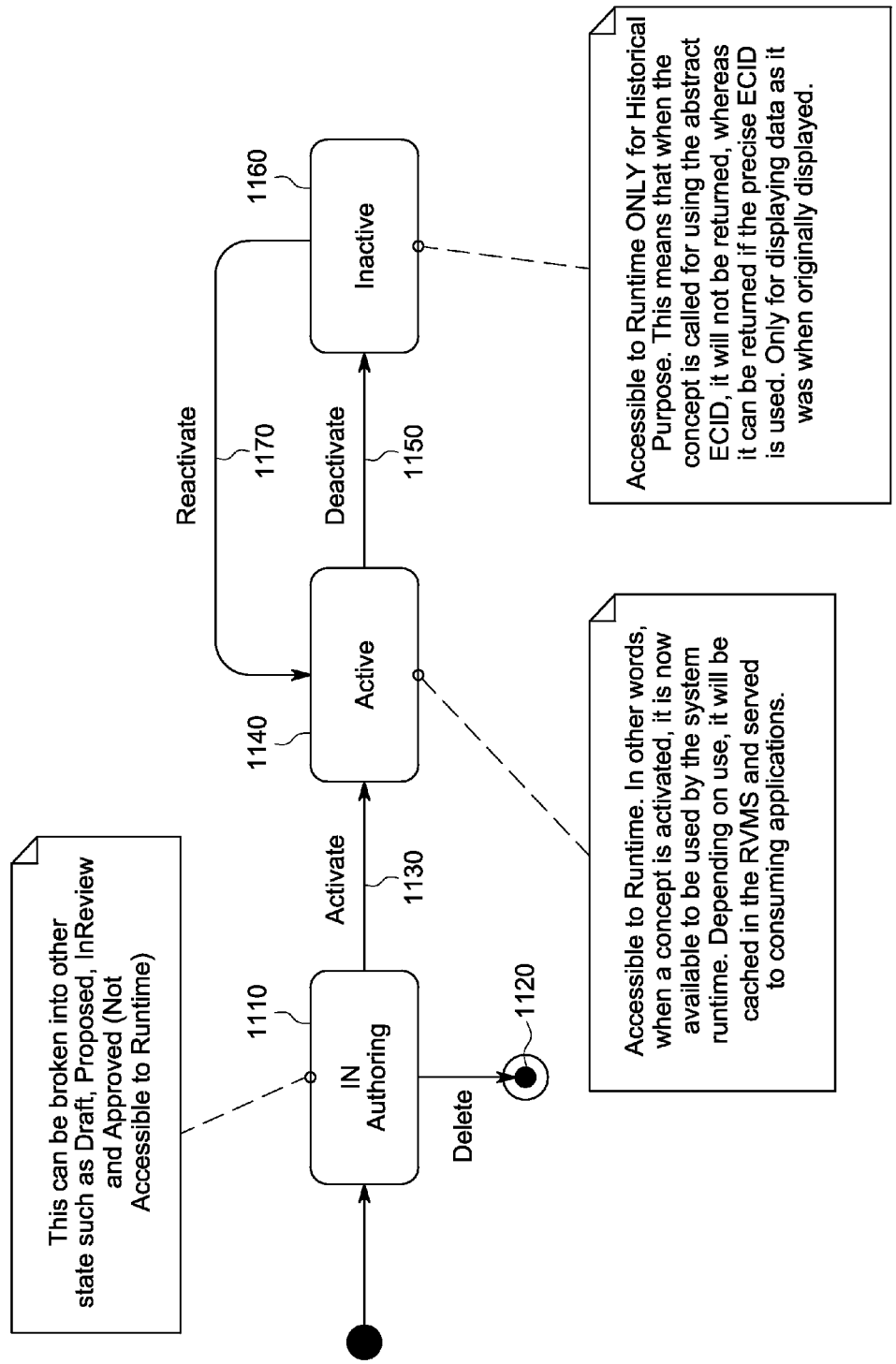
FIG. 11 depicts an example life cycle of a concept.

The life cycle of a concept is as displayed in FIG. 11. While in an authoring state 1110, there may be multiple other states a concept passes through, such as Draft, Proposed, In Review, Approved, etc. (state may be configurable, for example). As illustrated for example in FIG. 11, there is a difference between state(s) "In Authoring" 1110 and state "Inactive" 11160. A concept "In Authoring" 1110 is not available to a system runtime, for example.

As shown in FIG. 11, a concept in Authoring 1110 can be deleted 1120. A concept can also be activated 1130 from Authoring 1110 and stored as Active 1140. When a concept is activated 1130, the concept is available to be used by the system runtime. Depending upon use, for example, the concept can be cached in the Runtime Vocabulary Management Services and served to consuming applications.

When a concept is deactivated 1150, the concept in the Inactive state 1160 remains in an Active Data Store available to the system runtime for historical purposes only—remaining accessible only by the precise ECID that identifies the specific concept version, for example. An Inactive concept can be reactivated 1170 to be placed back in the Active state 1140.

Runtime Vocabulary Management Services (RVMS) 1030 refers to a portion of vocabulary data that is cached to provide a repository of data from the AVMS 1020 to improve performance for runtime applications 1042. The RVMS 1030 provides an in-memory cache 1036 to allow quick lookup access to terminology. The cache 1036 can be persisted in a persistent data store 1037 (i.e. Database) and can re-load the in-memory cache 1036 when the application is re-started. Data can be pulled into the Runtime 1031 from the AVMS 1020 on demand, for example.

In an example, components defined in the logical group of Runtime Vocabulary Management Services 1030 include CTS (e.g., CTS 1.2) Vocabulary Runtime services 1031 (with runtime operations 1032), plus other involved services, and a caching layer (implemented by a cache manager 1034 communicating with caches on demand 1035, an in memory cache 1036, and a persistent cache 1037) which resides on top of the Active Vocabulary Data Store. The RVMS CTS vocabulary runtime 1031 can interface with content deployment 1040, interoperability HL7 messaging 1041, and/or applications 1042 via runtime operations 1032. The vocabulary runtime 1031 can also receive input from RVMS CTS extensions 1033. Applications 1042 and/or interoperability messaging 1041 can communicate with the cache manager 1034 via RVMS code mapping 1038 and code mapping operations 1039, for example.

Core consumers of the RVMS 1030 include content deployment and packaging, Interoperability Foundation (HL7 messaging translation), and clinical applications in general, for example. Content Deployment and Packaging use the RVMS sub-system 1030 in order to pre-resolve terminology references (ECIDs) in the content, and in order to prepare the cache for terminology dependencies of newly deployed content, for example. Interoperability can use this sub-system to translate ECIDs from HL7 messages to text, and/or translate external codes to ECIDs and then ECIDs to text, for example. The translation from external code to ECID can occur in the CTS Vocabulary Runtime Operations 1031 implementation to help make the API seamless.

Terminology Repositories can be modeled and stored using Mayo Clinic's LexGrid, for example. A set of biomedical informatics grid (BIG) enterprise vocabulary services (EVS) adapters can be used to store and/or retrieve terminology metadata. For example, a collection of programmable interfaces provided by LexBIG/LexEVS (further referred to as LexEVS) from the Mayo Clinic can be used as the software API, including a relational database management system (RDBMS) implementation, used to access data in the Terminology Repositories. Compliant CTS interfaces are created and maintained as part of an ECIS Terminology Services Foundation to fulfill CTS compliance requirements and to abstract and maintain loose coupling with LexEVS API.

Figure 12:
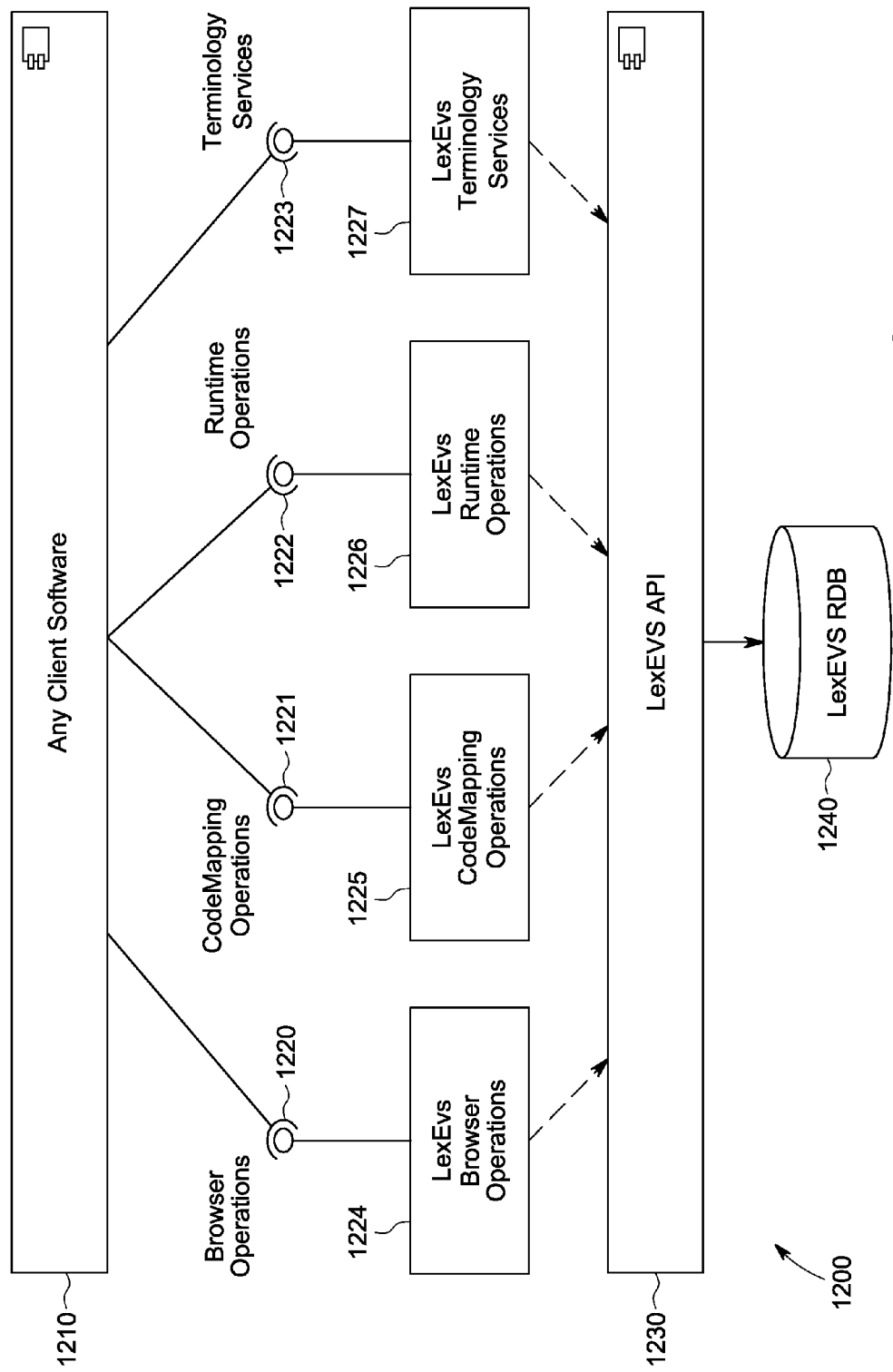
FIG. 12 depicts an example class diagram illustrating how LexEVS is used for CTS and/or other Terminology Services implementation.

FIG. 12 depicts an example class diagram illustrating how LexEVS is used for CTS and/or other Terminology Services implementation. In the system 1200, client software 1210 can interact with the relational database (e.g., LexEVS RDB) 1240 via an Application Programming Interface (e.g., LexEVS API) 1230 and a plurality of operations 1220-1227. Operations include browser operations 1220 (such as browser operations 1010, 1017, and/or 1022 of FIG. 10), code mapping operations 1221 (such as code mapping operations 1012 and/or 1039 of FIG. 10), runtime operations 1222 (such as runtime operations 1032 of FIG. 10), and terminology services 1223, which communicate with LexEVS browser operations 1224, LexEVS code mapping operations 1225, LexEVS runtime operations 1226, and LexEVS terminology services 1227, respectively. The LexEVS operations 1224-1227 communicate with the API 1230 to retrieve and/or deposit information in the RDB 1249.

Figure 13:
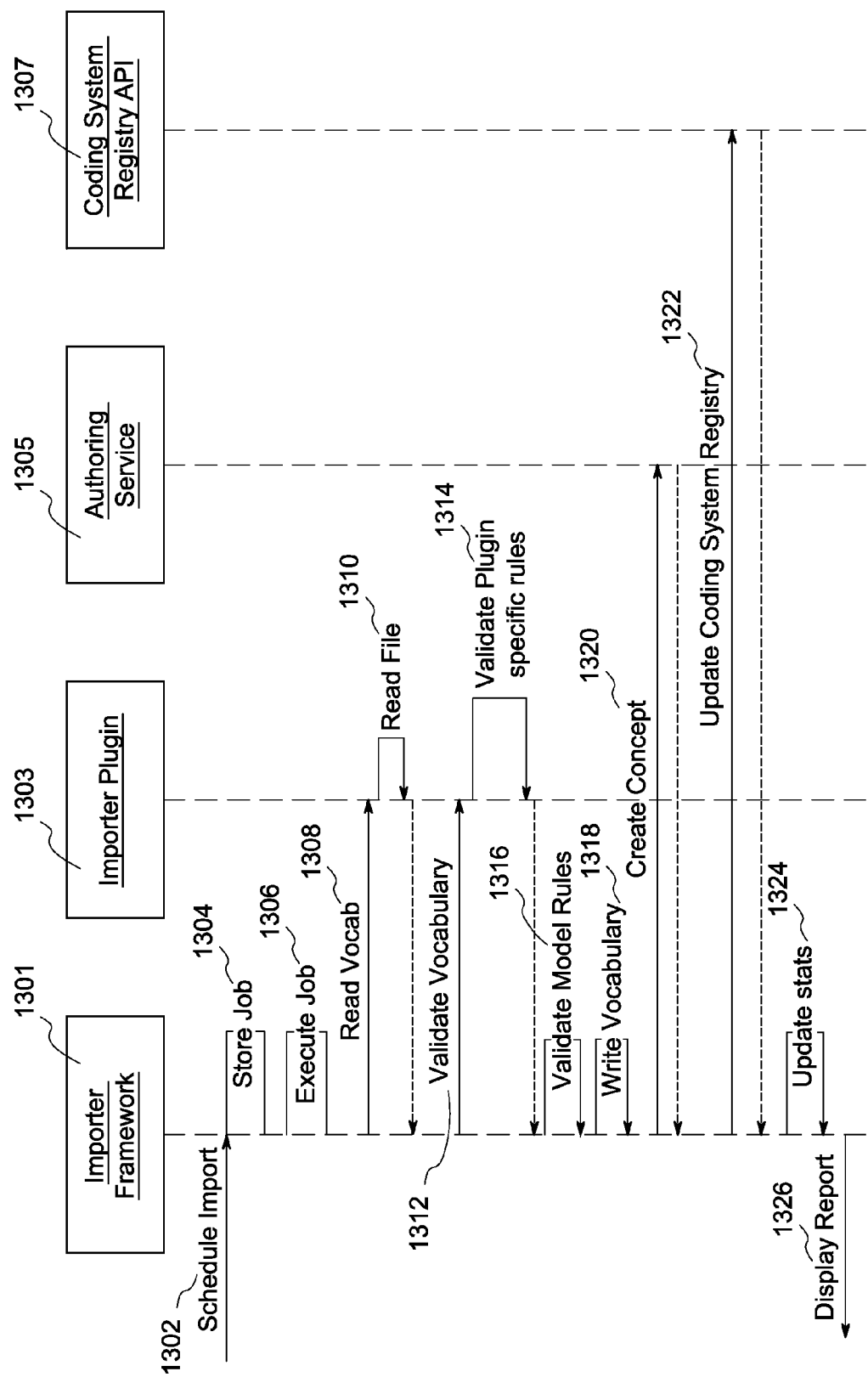
FIG. 13 illustrates an example use of the CVMS to import external code systems, author codes for use in ECIS, and/or manage concept lifecycle.

As illustrated, for example, in FIG. 13, the CVMS 1001 can be used to import external code systems, author codes for use in ECIS, and/or manage concept lifecycle. The data flow 1300 depicts an example high level importing sequence to import an external vocabulary into the CVMS 1001. At 1302, a terminology code import is scheduled via an importer framework 1301 (such as the importer framework 1002 of FIG. 10). At 1304, the import job is stored, and, at 1306, the import job is executed via the importer framework 1301.

At 1308, an instruction to read a vocabulary is transmitted from the importer framework 1301 to an importer plugin 1303 (such as the importer plugin 1003 of FIG. 10). At 1310, a retrieved vocabulary file is read using the importer plugin 1303. At 1312, the vocabulary is validated between the importer plugin 1303 and the importer framework 1301. At 1314, plugin-specific rules are validated. At 1316, model rules are validated. Then, at 1318, the vocabulary is written at the importer framework 1301.

At 1320, a concept is created using the vocabulary and passed to the authoring service 1305 (such as the authoring service 1008 of FIG. 10). At 1322, a coding system registry is updated via a coding system registry API 1307 (such as the code system registry API 1007 of FIG. 10). At 1324, statistics are updated at the importer framework 1301. Then, at 1326, a report is displayed to a user via the importer framework 1301.

Figure 14:
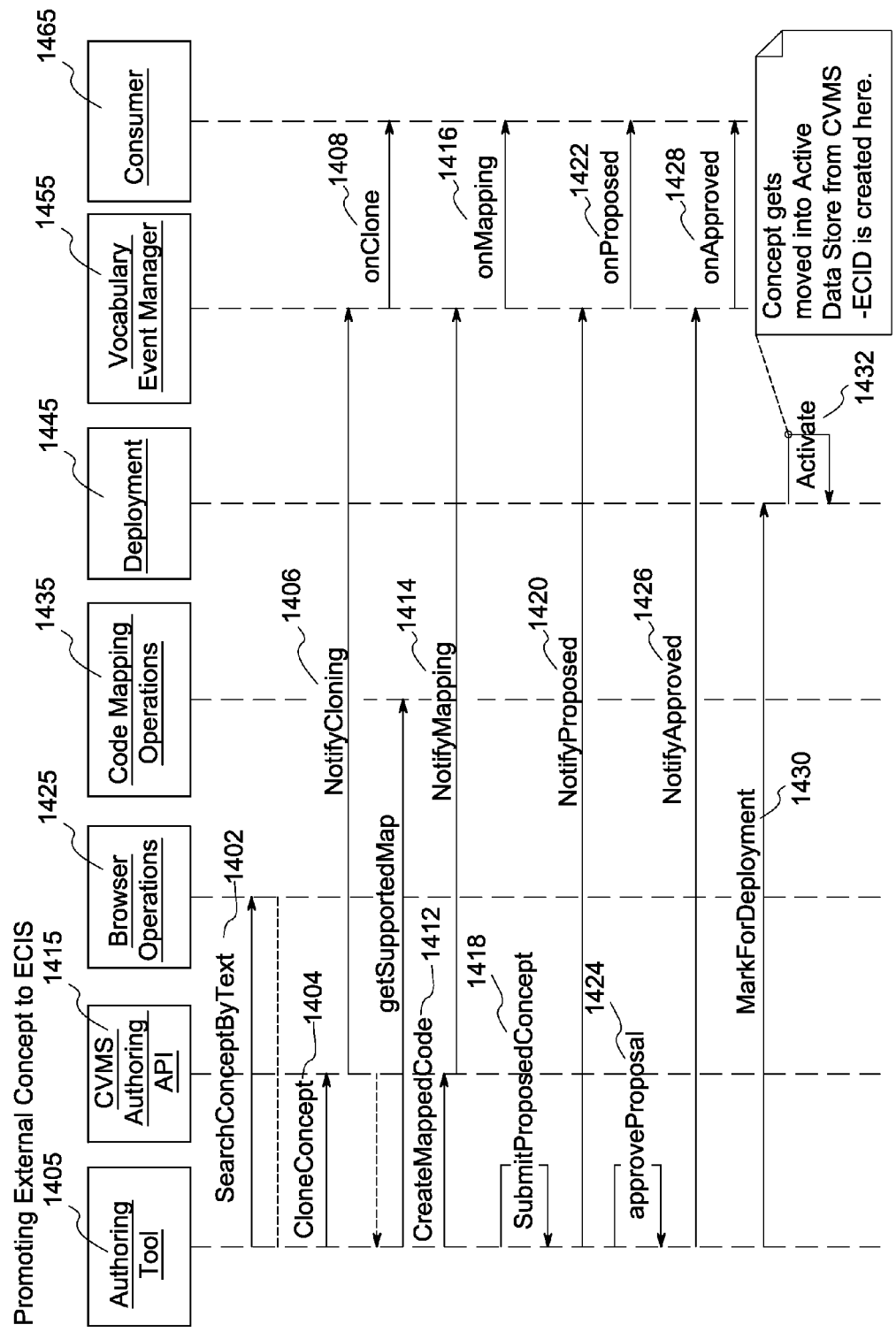
FIG. 14 illustrates an example sequence to promote an externally imported concept to an ECIS namespace and to activation.

FIG. 14 illustrates an example sequence 1400 to promote an externally imported concept to an ECIS namespace and to activation. At 1402, a concept generated from an authoring tool 1405 (such as the authoring tool 1015 of FIG. 10) is searched by text using browser operations 1425 (such as the browser operations 1009 and/or 1010 of FIG. 10). At 1404, the concept is cloned or copied via the CVMS authoring API 1415 (such as the authoring API 1008 of FIG. 10). At 1406, a vocabulary event manager 1455 (such as the vocabulary event manager 1014 of FIG. 10) is notified of the concept cloning. The clone is passed to a consumer 1465 (such as the consumer 1016 of FIG. 10) at 1408, for example.

At 1410, a supported mapping is retrieved from code mapping operations 1435 (such as code mapping operations 1011 and/or 1012 of FIG. 10). At 1412, the authoring tool 1405 creates mapped code. At 1414, the vocabulary event manager 1455 is notified of the mapping by the CVMS authoring API 1415. Upon mapping, at 1416, the mapping is provided by the vocabulary event manager 1455 to the consumer 1465.

At 1418, a proposed concept is submitted via the authoring tool 1405. At 1420, the vocabulary event manager 1455 is notified of the proposal via the authoring tool 1405. At 1422, the proposal is communicated from the vocabulary event manager 1455 to the consumer 1465.

At 1424, the proposal is approved via the authoring tool 1405. At 1426, notification of the concept approval is sent from the authoring tool 1405 to the vocabulary event manager 1455. Upon approval 1428, notice is sent to the consumer 1465.

At 1430, the approved concept is marked for deployment 1445 (such as the content deployment 1040 of FIG. 10). At 1432, the concept is activated. For example, the concept is moved into an active data store from the CVMS and an ECID can be created.

In an example, using Mayo Clinic's LexEVS product, a persistence layer used by the importers is a combination of LexEVS code reuse and extensions to override and extend functionality. Model object(s) used can include Eclipse Modeling Framework (EMF) object, for example. In an example, parts of the model to be persisted at a time, rather than requiring the entire model to be populated and persisted.

In an example, the HL7 Importer reads from the HL7 Model Interchange Format (MIF) in XML, using a Streaming API for XML (StAX) to stream the input XML file, removing a need to hold the entire vocabulary in memory at once when extracting.

Figure 15:
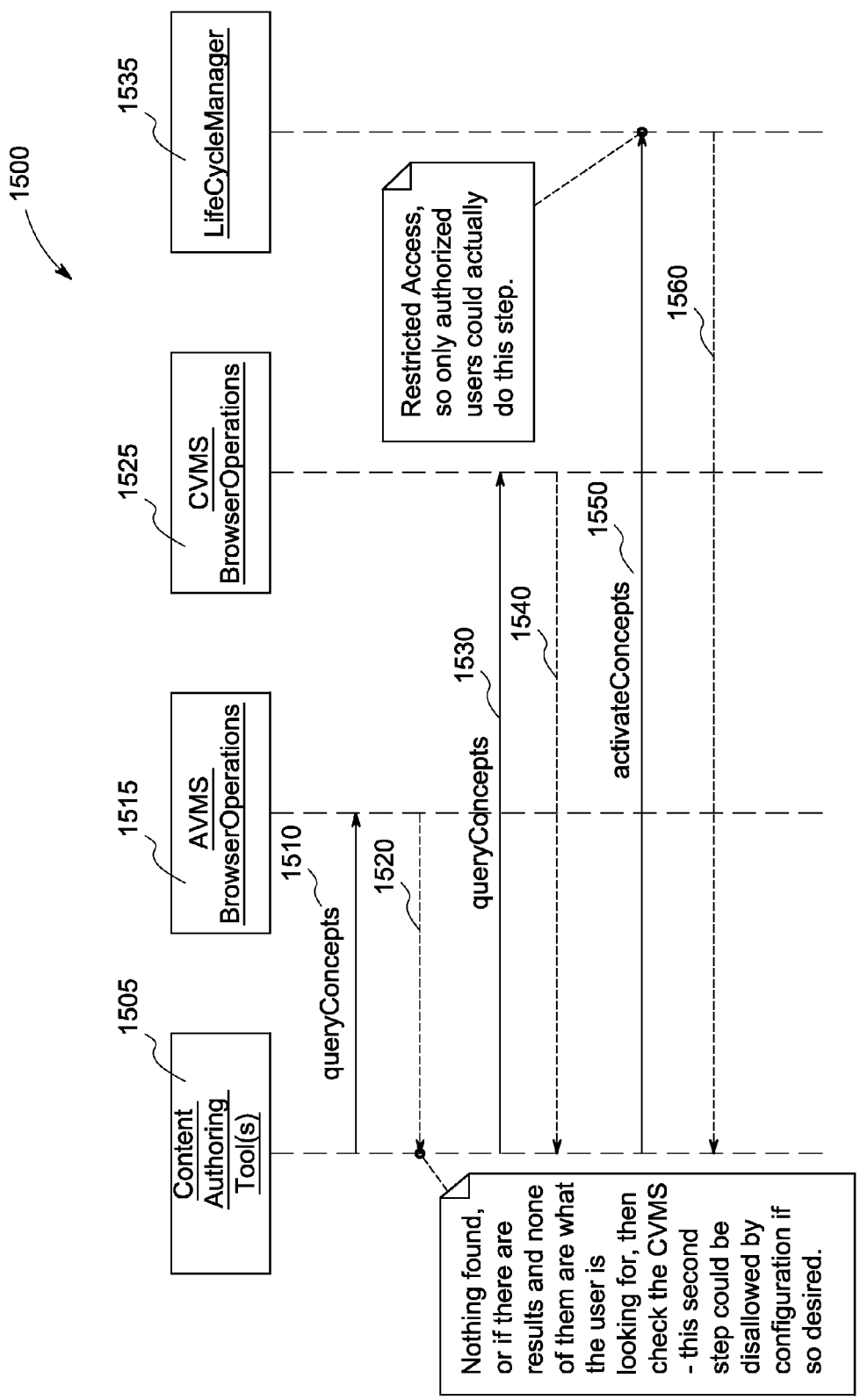
FIG. 15 illustrates an example sequence to browse a consolidated vocabulary store and activate desired concept(s) and/or concept update(s).

The AVMS stores and provides access to browse the Active set of terminology authored for and used within ECIS, for example. FIG. 15 illustrates an example sequence 1500 to browse a consolidated vocabulary store and activate desired concept(s) and/or concept update(s). For example, when content authoring tool(s) are unable to find vocabulary data in the Active set, then authorized user(s) can browse the consolidated store and activate (or propose activation based on workflow) the desired concept(s) and/or concept update(s). A system configuration could limit this to just being able to query the active store, for example.

As illustrated, for example, in FIG. 15, at 1510, one or more content authoring tools 1505 (such as content authoring tools 1015 of FIG. 10) are used to query one or more concepts via AVMS browser operations 1515 (such as AVMS browser operations 1021 of FIG. 10). At 1520, If nothing is found or if none of the available results meet user criteria, then the content authoring tool(s) 1505 can be used to query CVMS browser operations 1525 (such as CVMS browser operations 1009 and/or 1010 of FIG. 10) at 1530. At 1540, results are returned from the CVMS browser operations 1525 to the content authoring tool(s) 1505. In an example, checking of the CVMS can be disallowed by configuration.

At 1550, one or more concepts are activated via a lifecycle manager 1535 (such as the lifecycle manager 1013 of FIG. 10). An acknowledgement and/or other result can be communicated back to the content authoring tool(s) at 1560, for example.

Figure 16:
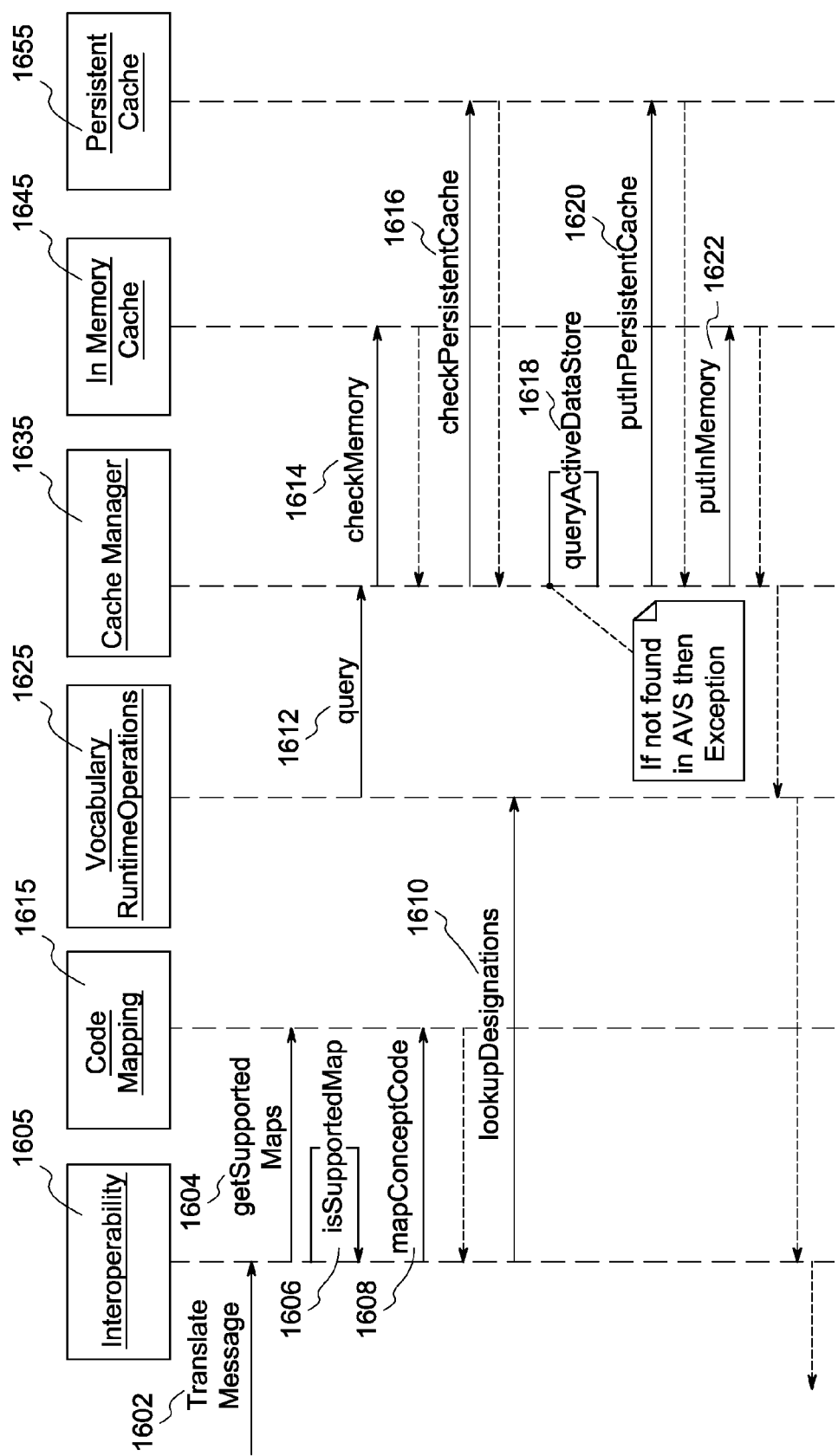
FIG. 16 illustrates an example data sequence to translate an HL7 message with an external code for which the system has mapped a corresponding ECIS code.

The RVMS serves as an entry point to access Active terminology at runtime, for example. The RVMS can serve as a caching manager, for example. As shown, for example, in FIG. 16, an HL7 message is translated with an external code for which the system has mapped a corresponding ECIS code.

At 1602, a message to be translated is provided to an interoperability module 1605 (such as the interoperability module 1041 of FIG. 10). At 1604, supported mappings are retrieved by the interoperability module 1605 from a code mapping module 1615 (such as the code mapping module 1038 of FIG. 10), and a result is returned to interoperability 1605. At 1606, the interoperability module 1605 determines whether a mapping is supported. If so, at 1608, concept code is mapped and returned to the interoperability module 1605.

At 1610, interoperability 1605 looks up designations from vocabulary runtime operations 1625 (such as vocabulary runtime operations 1031 and/or 1032 of FIG. 10). At 1612, the vocabulary runtime operations 1625 queries a cache manager 1635 (such as cache manager 1034 of FIG. 10). At 1614, the cache manager 1635 checks memory in an in memory cache 1645 (such as in memory cache 1036 of FIG. 10) for the designation(s). If information is found, it is returned to the cache manager 1635. At 1616, the cache manager 1635 checks a persistent cache 1655 (such as persistent cache 1037 of FIG. 10) and received query results (if any) from the persistent cache 1655.

At 1616, the cache manager 1635 queries the active data store. If the information is not found, then an exception can be triggered. If the queried information is found, then, at 1620, the results are placed in the persistent cache 1655. At 1622, the information is also placed in the in memory cache 1645. Results can then be passed to the vocabulary runtime operations 1625, code mapping 1615, and/or interoperability 1605, as well as a user (e.g., a human and/or electronic user), for example.

Figure 17:
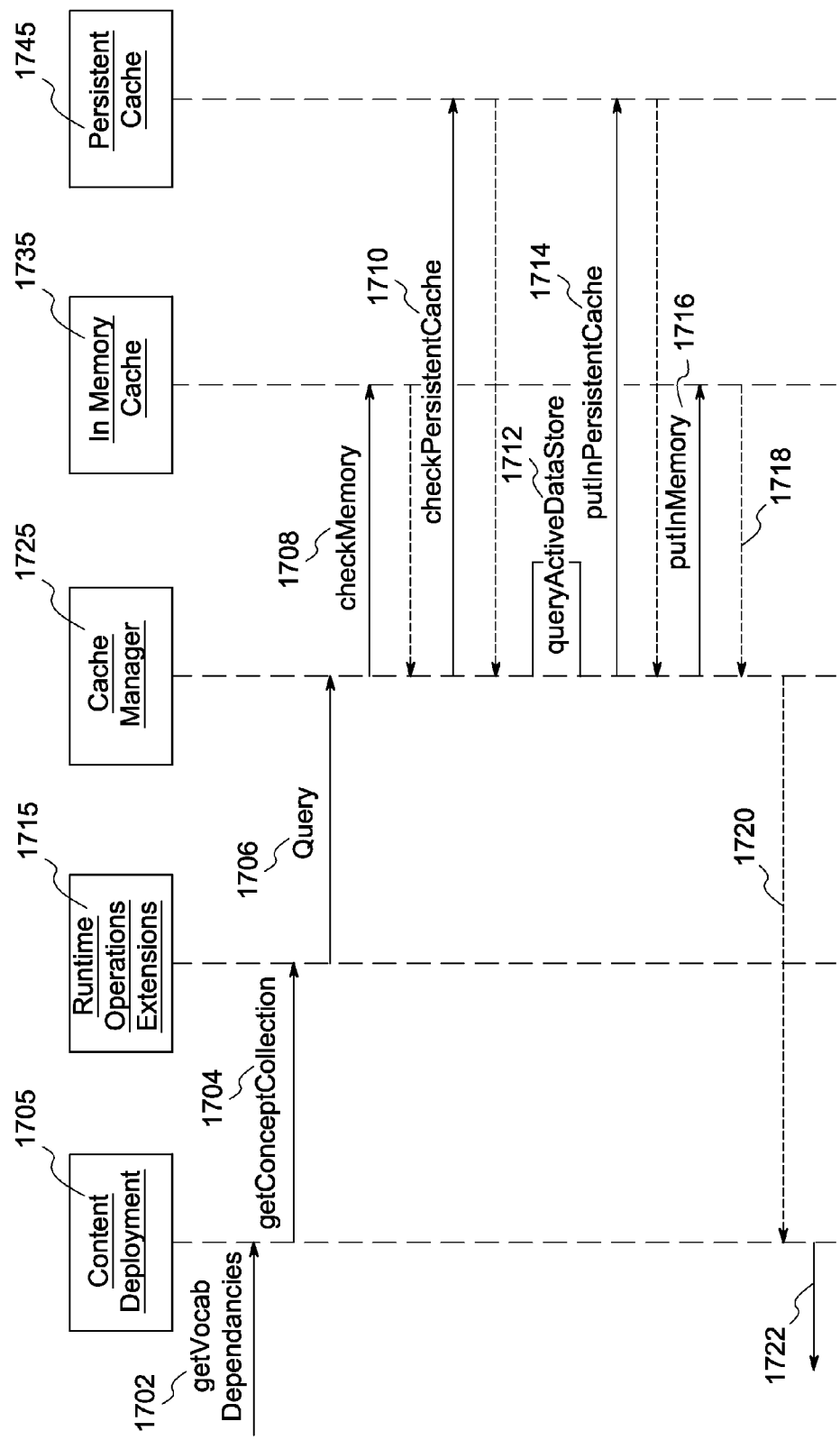
FIG. 17 illustrates an example data sequence for content deployment to "prime" the cache and/or resolve vocabulary dependency in bulk.

FIG. 17 illustrates an example data sequence 1700 for content deployment to "prime" the cache and/or resolve vocabulary dependency in bulk. At 1702, vocabulary dependencies are retrieved from a content deployment module 1705 (such as the content deployment 1040 of FIG. 10). At 1704, a related concept collection is retrieved by content deployment 1705 from a runtime operations extensions module 1715 (such as RVMS extension module 1033 of FIG. 10).

At 1706, a query is formed and sent by runtime operations extensions 1715 to a cache manager 1725 (such as the cache manager 1034 of FIG. 10). At 1708, the cache manager 1725 checks memory at an in memory cache 1735 (such as the in memory cache 1036 of FIG. 10) in relation to the query, and applicable results are returned to the cache manager 1725. At 1710, the cache manager 1725 checks a persistent cache 1745 (such as the persistent cache 1037 of FIG. 10), and applicable results are returned to the cache manager 1725.

At 1712, the cache manager 1725 queries the active data store. At 1714, query results are place in the persistent cache 1745. At 1716, query results are placed in the in memory cache 1735. At 1718, results are provided to the cache manager 1725, and, at 1720, results are provided to content deployment 1705. At 1722, results are provided to a user (e.g., a human and/or electronic user).

In an example, vocabulary content events, such as updates, activations, etc., are managed for external entities as well as other components of the system. For example, when terminology that is being consumed by content (such as CEMs) is changed, the change is communicated to content administrator(s)/author(s) using one or more event managers.

In another example, dependency notification can be supported by searching for and identifying dependencies and checking content changes. For example, a CEM editor can search, as part of validation, the concept(s) it uses, check for changes, and then provide a warning to the author if there are changes (including a link to a view of the new changes, for example). Alternatively and/or in addition, a terminology author can search for one or more CEMs with references to a certain concept, a package, and/or other grouping of concepts, for example.

In an example, to be able to easily add importers for more code systems and versions/formats that can change over time, a framework is provided for importer pluggability. For example, CVMS can provide a pluggable framework for importing external vocabularies. Compatibility of an importer plug-in can be validated by the framework. Compatibility can be defined by the version of the framework and the versions of any significant dependencies (e.g., services, data store, etc), for example.

In an example, an importer can provide a view of changes between one version of a coding system and another version of the same coding system (e.g., a "diff").

In an example, some content authoring tools, such as for CEM, can be fully integrated with the authoring of Terminology. When creating a CEM, a concept can be automatically created along with the CEM. There also may be additional terminology needed for a CEM that a modeler can add based on privileges, etc.

Clinicians at different sites of the healthcare system often prefer different synonyms than those provided for various concepts, and want to be able to quickly add them without a controlled workflow. In an example, the system can distinguish between controlled vocabulary and local preference vocabulary. Additionally, properties that are specific to process, etc., for a site can be defined. In an example, an ability to create new concepts precedes a controlled process via a feature to request new terminology. In an example, local terminology can be made distinct from released controlled terminology.

In an example, CEM models are created to define certain types of concepts. For example, a CEM model can be created for a lab concept to specify what types and how many designations the concept will have, etc. The CEM model can then be used to facilitate cloning, authoring tool data entry forms, validation on import, etc. Furthermore, models can be placed in "groups" that are commonly created together.

In an example, modeling and management of concept designations includes support of internationalization or language variation.

Figure 18:
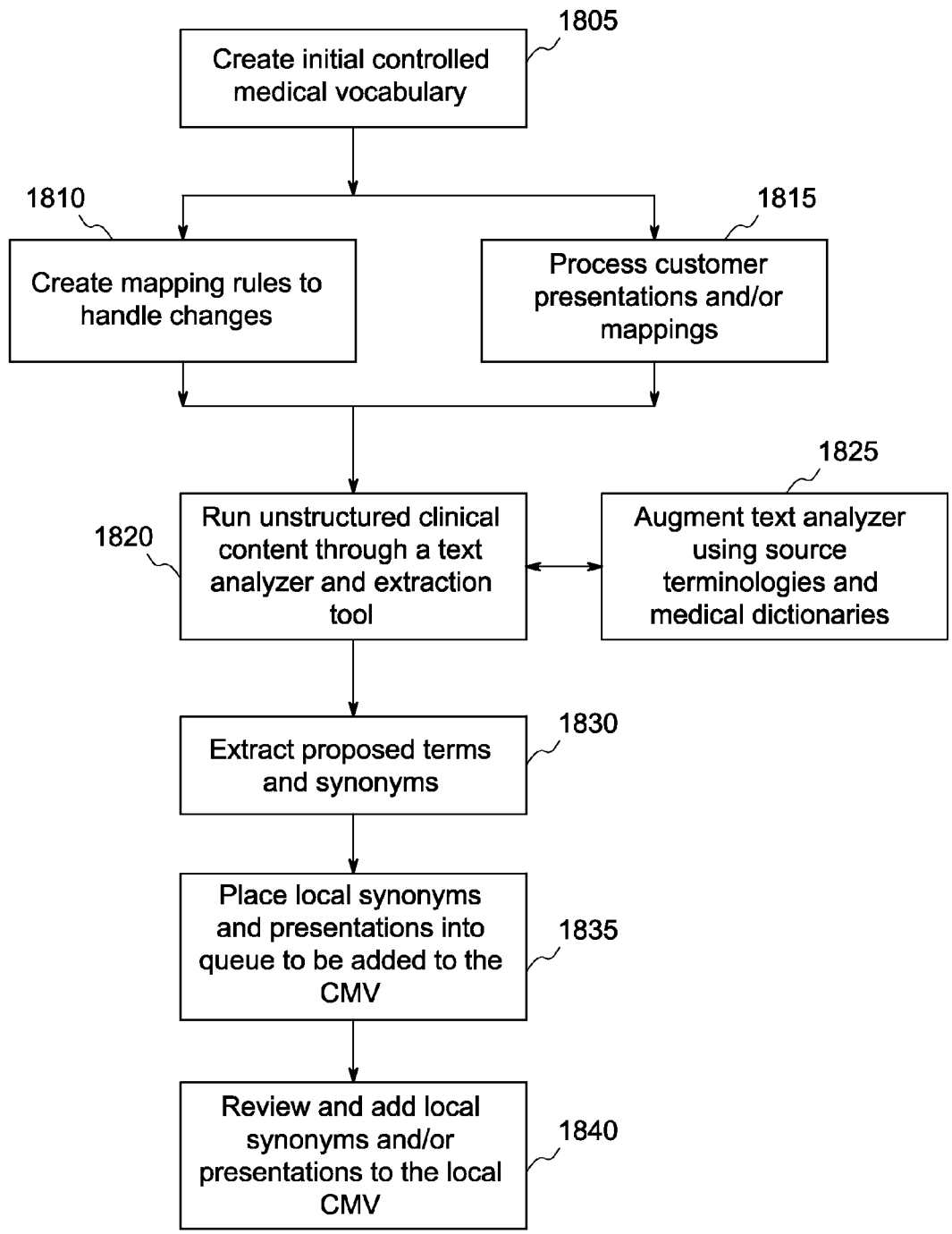
FIG. 18 is an example flow diagram for a method for supplementing a controlled medical vocabulary with localized clinical content.

FIG. 18 is a flow diagram for a method 1800 for supplementing a controlled medical vocabulary with localized clinical content. At 1805, an initial controlled medical vocabulary is created. For example, an initial CMV is created by cloning sections of external terminologies by healthcare data domain (e.g., LOINC for laboratory terminology, CPT for medical procedures, etc.). Standard terminology structure (e.g., relationships, concepts, and terms) are retained where applicable. Mappings between the CMV and publicly available mappings (e.g., ICD-9 to ICD-10, SNOMED to CPT, etc.) are then used to create a web of related data. The web of data includes both direct (e.g., equivalent) and indirect (e.g., is broader than, is narrower than, etc.) mappings.

At 1810, mapping rules are created to accommodate changes. For example, when a new term is added by a third party organization, the mapping for sister terms may specify to automatically propagate "additions" or put them into proposed status.

At 1815, alternatively or in addition to 1810, customer presentations and/or mappings are processed. For example, this is first accomplished by a healthcare organization aggregating its clinical content, including nursing, physician, and administrative documents.

At 1820, unstructured clinical content is passed through a text analyzer and extraction tool. For example, the text analyzer and extraction tool can organize the information based on synonym, abbreviation, relevance to existing source terminology, etc. At 1825, the text analyzer is augmented using one or more source terminologies and medical dictionaries. At 1830, proposed terms and synonyms are extracted. Proposals are put into a queue for a terminology engineer to validate and promote to the controlled medical vocabulary, for example. At 1835, local synonyms and presentations are placed into a queue to be added to the CMV. At 1840, local synonyms and presentations are reviewed and added to the local CMV.

Figure 19:
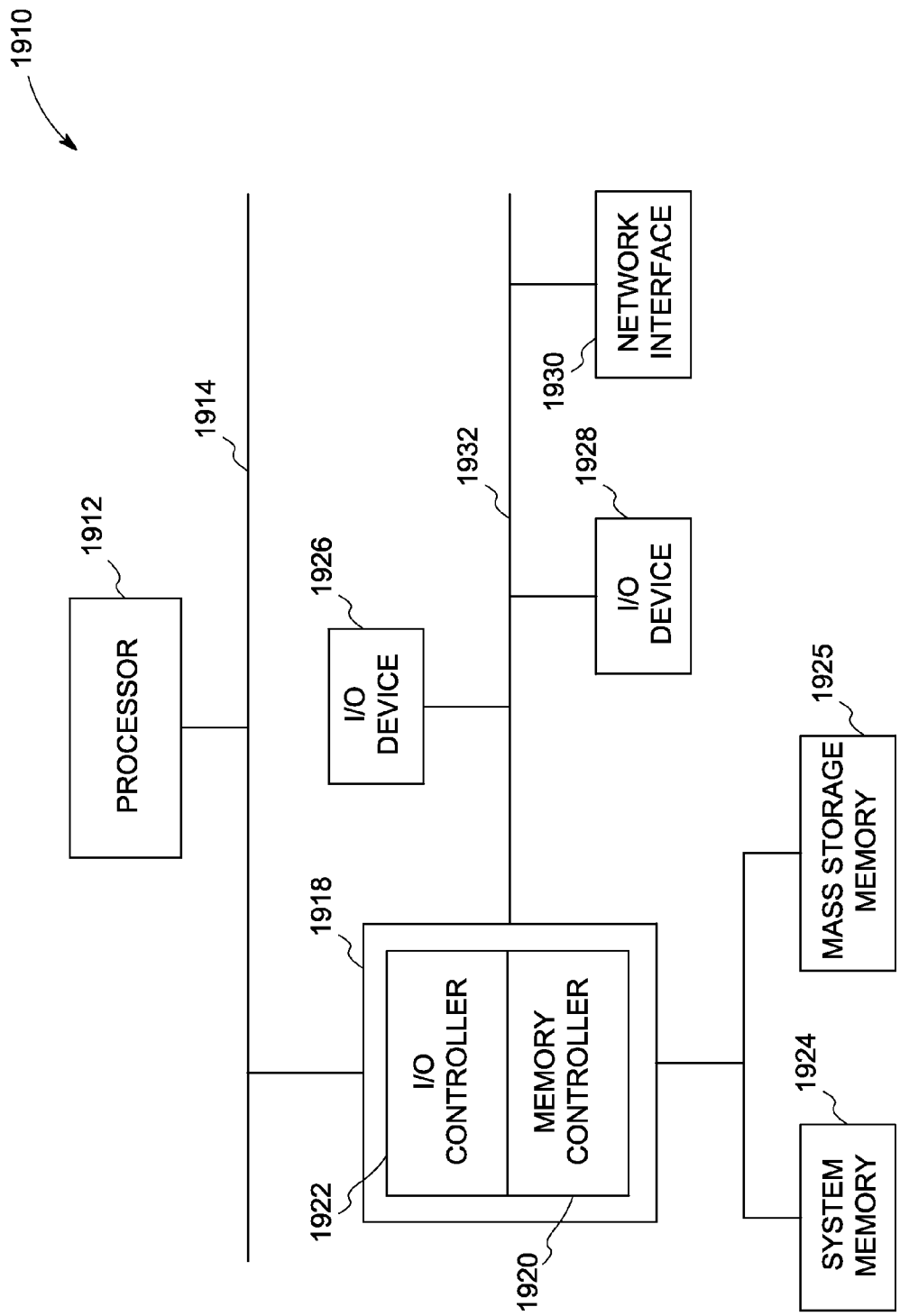
FIG. 19 is a block diagram of an example processor system that may be used to implement systems, apparatus, and methods described herein.

FIG. 19 is a block diagram of an example processor system 1910 that may be used to implement systems, apparatus, and methods described herein. As shown in FIG. 19, the processor system 1910 includes a processor 1912 that is coupled to an interconnection bus 1914. The processor 1912 may be any suitable processor, processing unit, or microprocessor, for example. Although not shown in FIG. 19, the system 1910 may be a multi-processor system and, thus, may include one or more additional processors that are identical or similar to the processor 1912 and that are communicatively coupled to the interconnection bus 1914.

The processor 1912 of FIG. 19 is coupled to a chipset 1918, which includes a memory controller 1920 and an input/output ("I/O") controller 1922. As is well known, a chipset typically provides I/O and memory management functions as well as a plurality of general purpose and/or special purpose registers, timers, etc. that are accessible or used by one or more processors coupled to the chipset 1918. The memory controller 1920 performs functions that enable the processor 1912 (or processors if there are multiple processors) to access a system memory 1924 and a mass storage memory 1925.

The system memory 1924 may include any desired type of volatile and/or non-volatile memory such as, for example, static random access memory (SRAM), dynamic random access memory (DRAM), flash memory, read-only memory (ROM), etc. The mass storage memory 1925 may include any desired type of mass storage device including hard disk drives, optical drives, tape storage devices, etc.

The I/O controller 1922 performs functions that enable the processor 1912 to communicate with peripheral input/output ("I/O") devices 1926 and 1928 and a network interface 1930 via an I/O bus 1932. The I/O devices 1926 and 1928 may be any desired type of I/O device such as, for example, a keyboard, a video display or monitor, a mouse, etc. The network interface 1930 may be, for example, an Ethernet device, an asynchronous transfer mode ("ATM") device, an 802.11 device, a DSL modem, a cable modem, a cellular modem, etc. that enables the processor system 1910 to communicate with another processor system.

While the memory controller 1920 and the I/O controller 1922 are depicted in FIG. 19 as separate blocks within the chipset 1918, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a machine accessible or readable medium and executable by, for example, a processor system (e.g., the example processor system 1910 of FIG. 19). When any of the appended claims are read to cover a purely software and/or firmware implementation, at least one of the components is hereby expressly defined to include a tangible medium such as a memory, DVD, CD, etc. storing the software and/or firmware.

FIGS. 4-7 and 13-18 include flow and/or data sequence diagrams representative of machine readable and executable instructions or processes that can be executed to implement the example systems, apparatus, and article of manufacture described herein. The example processes of FIGS. 4-7 and 13-18 can be performed using a processor, a controller and/or any other suitable processing device. For example, the example processes of FIGS. 4-7 and 13-18 can be implemented in coded instructions stored on a tangible medium such as a flash memory, a read-only memory (ROM) and/or random-access memory (RAM) associated with a processor (e.g., the processor 1912 of FIG. 19). Alternatively, some or all of the example processes of FIGS. 4-7 and 13-18 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 4-7 and 13-18 can be implemented manually or as any combination(s) of any of the foregoing techniques, for example, any combination of firmware, software, discrete logic and/or hardware. Further, although the example processes of FIGS. 4-7 and 13-18 are described with reference to the flow diagrams of FIGS. 4-7 and 13-18, other methods of implementing the processes of FIGS. 4-7 and 13-18 can be employed. For example, the order of execution of the blocks may be changed, and/or some of the blocks described may be changed, eliminated, sub-divided, or combined. Additionally, any or all of the example processes of FIGS. 4-7 and 13-18 can be performed sequentially and/or in parallel by, for example, separate processing threads, processors, devices, discrete logic, circuits, etc.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Thus, certain examples described herein facilitate use of reduced manpower associated with manually maintaining the CMV, as well as helping to provide faster product installation time. Certain examples eliminate a need to purchase content from a third party content provider or consultancy (e.g., 3M, Apelon, Health Language, etc.). Certain examples provide an ability for customers to be able to contribute to a centrally managed CMV. Certain examples provide technical effects of advanced analytics, real-time decision support, and business intelligence through use of structured, coded data. Certain examples store high quality, computationally comparable, reliable, and reusable data and improve internal and external interoperability of systems, processes, and data. Certain examples help reduce costs incurred due to redundant and disparate data definition, storage, and maintenance and help promote national and international interoperability by sharing terminology with the healthcare community at large.

Certain examples described herein take advantage of text based analysis and linguistics to map a customer's vocabulary to a backbone code system. Conversely, vendors currently force a terminology onto their customers or disregard the standards. Certain examples provide a technical effect by analyzing healthcare terminology providers' data using an algorithm to rank the granularity of a medical term (e.g., simpler words have smaller number of letters), the popularity of a term (how often is the term used by the organization), and the relationship to similar terms (informed by semantic proximity, other medical publications and external dictionaries, etc.). This analysis results in proposals of where to place the provider's data in the CMV.

Certain examples can be used in a management and visualization tool to create local extensions/presentations to a CMV. In addition to the tool, certain examples include a series of vocabulary importers, text based algorithms, workflow engine, data store, translation tables, and terminology services. Certain examples provide automated mapping and workflow facilitation/management, etc. Certain examples provide a repository or message inbox for user review of terminology as well.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method to provide clinical terminology services, said method comprising:
accessing an initial controlled medical vocabulary including at least one external terminology via a vocabulary management server;
processing local clinical content including unstructured local clinical content provided via an importer framework;
analyzing and extracting the unstructured local clinical content using a text analyzer and extraction tool to generate one or more proposed terms by:
ranking a granularity of a medical term;
determining a popularity of a term; and
evaluating a relationship to similar terms, wherein analyzing results in one or more proposals regarding where to place the local clinical content and representations of the local clinical content in the controlled medical vocabulary;
identifying one or more synonyms for the one or more proposed terms;
placing the one or more synonyms into a queue to be added to the controlled medical vocabulary;
reviewing the one or more synonyms placed into the queue; and
adding the one or more synonyms to the controlled medical vocabulary with placement and relationship based on analyzing and extracting unstructured local clinical content to automatically map between the at least one external terminology and the local clinical content to supplement the controlled medical vocabulary with the local clinical content and provide the controlled medical vocabulary to one or more vocabulary consumers.

2. The method of claim 1, where the text analyzer and extraction tool uses source terminologies and medical dictionaries.

3. The method of claim 1, further comprising creating mapping rules to accommodate changes to the initial controlled medical vocabulary.

4. The method of claim 1, wherein the mapping rules comprise at least one of an automated concept mapping rule, an inferred concept mapping rule, and an automated matching of mappings and relationships.

5. The method of claim 1, further comprising processing at least one of local customer presentations and mappings.

6. The method of claim 1, wherein the controlled medical vocabulary spans organizations.

7. The method of claim 1, wherein the controlled medical vocabulary is mapped according to one or more standards to facilitate interoperability and the use of localized terms.

8. The method of claim 1, wherein reviewing the one or more synonyms placed into the queue further comprises reviewing the one or more synonyms using an integrated automated workflow for computer review of the one or more synonyms and a human workflow for manual review of at least a portion of the one or more synonyms.

9. The method of claim 8, wherein the human workflow comprises manual human review of a least a portion of the one or more synonyms via an electronic message inbox.

10. A clinical terminology services system providing a controlled medical vocabulary, said system comprising:
an importer framework accessing an initial controlled medical vocabulary including at least one external terminology;
a vocabulary management server including terminology modeler and mapper to process local clinical content represented by one or more clinical models including unstructured local clinical content, the terminology modeler and mapper including a text analyzer and extraction tool to extract and analyze the unstructured local clinical content using a text analyzer and extraction tool to generate one or more proposed terms, the vocabulary management server facilitating identifying one or more synonyms for the one or more proposed terms, placing the one or more synonyms into a queue to be added to the controlled medical vocabulary, and reviewing the one or more synonyms placed into the queue, the vocabulary management server adding the one or more synonyms to the controlled medical vocabulary with placement and relationship based on analyzing and extracting unstructured local clinical content to automatically map between the at least one external terminology and the local clinical content to supplement the controlled medical vocabulary with the local clinical content wherein the text analyzer and extraction tool extracts and analyzes unstructured local content by:

ranking a granularity of a medical term;

determining a popularity of a term; and evaluating a relationship to similar terms, wherein analyzing results in one or more proposals regarding where to place the local clinical content and representations of the local clinical content in the controlled medical vocabulary.

11. The system of claim 10, where the text analyzer and extraction tool uses source terminologies and medical dictionaries.

12. The system of claim 10, wherein the vocabulary management server creates mapping rules to accommodate changes to the initial controlled medical vocabulary.

13. The system of claim 10, wherein the mapping rules comprise at least one of an automated concept mapping rule, an inferred concept mapping rule, and an automated matching of mappings and relationships.

14. The system of claim 10, wherein the vocabulary management server processes at least one of local customer presentations and mappings.

15. The system of claim 10, wherein the controlled medical vocabulary spans organizations.

16. The system of claim 10, wherein the controlled medical vocabulary is mapped according to one or more standards to facilitate interoperability and the use of localized terms.

17. The system of claim 10, wherein the vocabulary management server facilitates reviewing the one or more synonyms placed into the queue further comprises reviewing the one or more synonyms using an integrated automated workflow for computer review of the one or more synonyms and a human workflow for manual review of at least a portion of the one or more synonyms.

18. The system of claim 17, wherein the human workflow comprises manual human review of a least a portion of the one or more synonyms via an electronic message inbox.

19. The system of claim 10, wherein the vocabulary management server stores the controlled medical vocabulary in a consolidated vocabulary storage in association with consolidated vocabulary translation maps and a code system registry.

20. An article of manufacture comprising:

a computer readable storage medium; and executable program instructions embodied in the computer readable storage medium that, when executed by a computer processor, cause the computer to implement a method to provide clinical terminology services, said method comprising:

accessing an initial controlled medical vocabulary including at least one external terminology;

processing local clinical content including unstructured local clinical content;

analyzing and extracting the unstructured local clinical content using a text analyzer and extraction tool to generate one or more proposed terms by:

ranking a granularity of a medical term;

determining a popularity of a term; and evaluating a relationship to similar terms, wherein analyzing results in one or more proposals regarding where to place the local clinical content and representations of the local clinical content in the controlled medical vocabulary;

identifying one or more synonyms for the one or more proposed terms;

placing the one or more synonyms into a queue to be added to the controlled medical vocabulary;

reviewing the one or more synonyms placed into the queue; and adding the one or more synonyms to the controlled medical vocabulary with placement and relationship based on analyzing and extracting unstructured local clinical content to automatically map between the at least one external terminology and the local clinical content to supplement the controlled medical vocabulary with the local clinical content.

* * * * *

UNITED STATES PATENT AND TRADEMARK OFFICE
CERTIFICATE OF CORRECTION

| | | |
|---|---|---|
| PATENT NO. | : 8,260,779 B2 | Page 1 of 1 |
| APPLICATION NO. | : 12/561547 | |
| DATED | : September 4, 2012 | |
| INVENTOR(S) | : Hudgins et al. | |

It is certified that error appears in the above-identified patent and that said Letters Patent is hereby corrected as shown below:

In Column 11, Line 11, delete "At705," and insert -- At 705, --, therefor.

In Column 14, Line 36, delete "CMVS" and insert -- CVMS --, therefor.

In Column 15, Line 18, delete "11160." and insert -- 1160. --, therefor.

In Column 18, Line 20, delete "in an in" and insert -- in a --, therefor.

In Column 24, Line 52, in Claim 9, delete "of a least" and insert -- of at least --, therefor.

In Column 25, Line 13, in Claim 10, delete "content" and insert -- content, --, therefor.

In Column 26, Line 5, in Claim 18, delete "of a least" and insert -- of at least --, therefor.

Signed and Sealed this
Fifth Day of February, 2013

Teresa Stanek Rea
*Acting Director of the United States Patent and Trademark Office*